United States Patent [19]

Beckmann et al.

[11] Patent Number: 5,149,638
[45] Date of Patent: Sep. 22, 1992

[54] TYLOSIN BIOSYNTHETIC GENES TYLA, TYLB AND TYLI

[75] Inventors: Robert J. Beckmann, Indianapolis; Karen L. Cox, Martinsville; Eugene T. Seno, Indianapolis, all of Ind.

[73] Assignee: Eli Lilly and Company, Indianapolis, Ind.

[21] Appl. No.: 741,204

[22] Filed: Jul. 30, 1991

Related U.S. Application Data

[63] Continuation of Ser. No. 251,718, Sep. 29, 1988, abandoned.

[51] Int. Cl.$^5$ .................. C12P 19/62; C12P 19/34; C12N 1/21; C12N 15/52
[52] U.S. Cl. .................................... 435/76; 435/72; 435/91; 435/169; 435/172.3; 435/252.33; 435/252.35; 435/320.1; 435/252.3; 536/27
[58] Field of Search ............ 435/69.1, 71.1, 72, 435/91, 169, 76, 172.3, 252.33, 252.35, 252.3, 320.1, 886; 536/27; 935/6, 9, 22, 29, 59, 60, 61, 66, 75

[56] References Cited

U.S. PATENT DOCUMENTS 4,680,265 7/1985 Birmingham et al. ............ 435/172.3

FOREIGN PATENT DOCUMENTS 0238323 9/1987 European Pat. Off. .
0251510 1/1988 European Pat. Off. .
0254576 1/1988 European Pat. Off. .

OTHER PUBLICATIONS

Kirby and Hopwood, 1976, J. Gen. Microbiol. 97:1-14.
Baltz et al., 1982, Genentics and Biochemistry of Tylosin Production in *Trends in Antibiotic Research* (eds. Unezawa et al.; published by the Japan Antibiotics Research Association).
Feitelson et al., 1983, Mol. Gen. Genet. 190:394-398.
Hopwood et al., 1983, Trends in Biotech. 1(2):42-48.
Chater and Bruton, 1983, Gene 26:67-78.
Malpartida and Hopwood, 1984, Nature 309:462-464.
Hopwood et al., 1985, Nature 314:642-644.
De Main, 1985, Nature 314:577-578.
Seno and Hutchinson, 1986, The biosynthesis of tylosin and erythromycin: model system for studies of the genetics and biochemistry of antibiotic formation, in *The Bacteria, A Treatise on Structure and Function*, (eds. J. R. Sokatch and L. N. Ornston), vol. IX, *Antibiotic-Producing Streptomyces* (vol. eds: S. W. Queener and L. E. Day), Academic Press, Inc., Orlando, FL, pp. 231-279.
Stonesifer et al., 1986, Mol. Gen. Genet. 202:348-355.
Birmingham et al., 1986, Mol. Gen. Genet. 204:532-539.
Cox et al., *J. Nat. Prod.*, 49 971 (1986).
Fishman et al., *PNAS*, U.S.A., 84 8248 (1987).
Fishman et al., Mar. 1986, Poster Session of the American Society of Microbiologists (ASM) meeting in Washington, D.C.

Primary Examiner—Richard A. Schwartz
Assistant Examiner—Nancy Vogel
Attorney, Agent, or Firm—Amy E. Hamilton; Leroy Whitaker

[57] ABSTRACT

Provided are gene sequences encoding tylosin biosynthetic gene products. In particular, recombinant DNA vectors comprising DNA sequences encoding the tylA, tylB, tylI and tylG activities of *Streptomyces fradiae* are provided. Also provided are host cells transformed with the noted vectors and a method for increasing the tylosin-producing ability of a tylosin-producing organism.

28 Claims, 9 Drawing Sheets

TYLOSIN BIOSYNTHETIC GENES TYLA, TYLB AND TYLI

This application is a continuation of application Ser. No. 07/251,718, filed on Sep. 29, 1988, now abandoned.

SUMMARY OF THE INVENTION

The invention relates to novel DNA sequences that code for antibiotic biosynthetic gene products, recombinant DNA expression vectors, the products encoded by said genes, and transformed microbial host cells.

The invention further comprises a novel method for increasing the antibiotic-producing ability of an antibiotic-producing organism. The method involves transforming a microbial host cell with a DNA sequence that codes for the expression of a gene product of the invention.

The present invention represents a significant commercial exploitation of recombinant DNA technology in antibiotic-producing organisms such as streptomycetes. Previously, the development and exploitation of recombinant DNA technology has been limited, for the most part, to the expression of specific polypeptides in E. coli and, in some instances, mammalian cells. These advances led to the comparatively simple expression of heterologous gene products such as human insulin A and B chains, human proinsulin, human growth hormone, human protein C, human tissue plasminogen activator, bovine growth hormone, and other compounds of potential therapeutic value. In each case, heterologous gene expression is primarily independent of and does not interact with, take part in, or modulate operative biosynthetic pathways. Recombinant DNA technology now can be applied to improve selected biosynthetic pathways for the expression of increased yields of known or new antibiotics or antibiotic precursors.

Most recombinant DNA technology applied to streptomycetes and other antibiotic-producing organisms has been limited to the development of cloning vectors. Early attempts include the disclosures of Reusser U.S. Pat. No. 4,332,898 and Manis et al. U.S. Pat. Nos. 4,273,875; 4,332,900; 4,338,400; and 4,340,674. Transformation of streptomycetes was not disclosed or taught in these early references. Improved vectors showing greater potential for use in antibiotic-producing organisms were disclosed by Fayerman et al. in U.S. Pat. No. 4,513,086; Nakatsukasa et al. in U.S. Pat. Nos. 4,513,085 and 4,416,994; Malin et al. in U.S. Pat. No. 4,468,462; PCT International Application WO/79/01169; Bibb et al., 1980, in Nature 284:526; Thompson et al., 1980, in Nature 286:525; Suarez et al., 1980, in Nature 286:527; Malpartida et al., 1984, in Nature 309:462; Hershberger, 1982, in Ann. Reports on Fermentation Processes, 5:101-126 (G. T. Tsao, ed., Academic Press N.Y.); Hershberger et al., 1983, in Ann. N.Y. Acad. Sci. 413:31-46; and Larson and Hershberger, 1984, in J. Bacteriol. 157:314-317. These improved vectors contain markers that are selectable in streptomycetes, can be used to transform many important Streptomyces strains, and constitute the tools required for conducting more complicated gene cloning experiments.

One such experiment is reported by Hopwood et al., 1985, in Nature 314:642. Although Hopwood et al. reported the production of novel hybrid antibiotic pigments, the disclosure does not focus on increasing the antibiotic-producing ability or biosynthetic efficiency of a given host cell but instead describes the transferring of actinorhobin pigment biosynthetic genes from one Streptomyces strain to another.

The previously described references provided the background for research leading to studies of the Streptomyces genome. In particular, European Patent Application, EP A 0 238 323 (Publication No. 87302318.8, published Sep. 23, 1987) discloses a small portion of the Streptomyces fradiae genome. This portion of the genome comprises a gene cluster comprising several tylosin biosynthetic genes.

This latter work is described in S. E. Fishman et al., Proc. Nat'l. Acad. Sci., U.S.A., 84, 8248 (1987) and K. L. Cox, et al., J. Natural Products, 49 971 (1986). Fishman et al. describe the biosynthetic gene cluster which comprises the tylE, tylD, tylH, tylF, tylJ, tylC, tylK, tylL and tylM biosynthetic genes. Those researchers, however, were not able to define DNA sequences corresponding to the tylA, tylB, tylG and tylI biosynthetic genes. Mutations in these genes block tylactone biosynthesis (tylG), prevent the attachment or biosynthesis of all tylosin sugars (tylA) or just mycaminose (tylB), or block oxidation at the C-20 position of tylactone (tylI). These genes are responsible, therefore, for activities necessary in the early steps of biosynthesis of tylosin. See FIG. 1 in this regard.

In contrast to this previous work, the present invention provides an unexpected second biosynthetic gene cluster, physically removed from the cluster described in Fishman, et al. This cluster has been shown to comprise DNA sequences which complement tylG, tylB, tylA, and tylI mutations. Thus, there are provided DNA sequences encoding four tylosin biosynthetic gene products, tylA, tylB, a tylG, and tylI. The invention also provides novel recombinant DNA expression vectors, the gene products of the noted genes, and host cells transformed with vectors comprising these genes.

The present invention is particularly useful in that it allows for the commercial application of recombinant DNA technology to streptomycetes and other antibiotic-producing organisms. Because over half of the clinically important antibiotics are produced by streptomycetes, it is especially desirable to develop methods that are applicable to that industrially important group. The present invention provides such methods and allows for the cloning of genes both for increasing the antibiotic-producing ability as well as for the production of new antibiotics and antibiotic precursors in an antibiotic-producing organism.

The following terms, as defined below, are used to described the invention.

Antibiotic—a substance produced by a microorganism that, either naturally or with limited chemical modification, inhibits the growth of or kills another microorganism or eukaryotic cell.

Antibiotic Biosynthetic Gene—a DNA segment that encodes an activity, such as an enzymatic activity, or encodes a product that regulates expression of an activity, that is necessary for a reaction in the process of converting primary metabolites to antibiotic intermediates, which also can possess antibiotic activity, and then to antibiotics.

Antibiotic Biosynthetic Pathway—the entire set of antibiotic biosynthetic genes and biochemical reactions necessary for the process of converting primary metabolites to antibiotic intermediates and then to antibiotics.

Antibiotic-Producing Microorganism—any organism, including, but not limited to Actinoplanes, Actinomadura, Bacillus, Cephalosporium, Micromonospora, Penicillium, Nocardia, and Streptomyces, that either produces an antibiotic or contains genes that, if expressed, would produce an antibiotic.

Antibiotic Resistance-Conferring Gene—a DNA segment that encodes an activity that confers resistance to an antibiotic.

ApR—the ampicillin-resistance phenotype or gene conferring same.

Host Cell—an organism, including the viable protoplast thereof, that can be transformed with a recombinant DNA cloning vector.

Operation of Antibiotic Biosynthetic Pathway—the expression of antibiotic biosynthetic genes and the related biochemical reactions required for the conversion of primary metabolites into antibiotics.

Recombinant DNA Vector—any selectable and autonomously replicating or chromosomally integrating agent, including but not limited to plasmids and phages, comprising a DNA molecule to which additional DNA can be or has been added, and which also can include DNA sequences necessary for the expression of the inserted additional DNA.

Restriction Fragment—any linear DNA generated by the action of one or more restriction enzymes.

Sensitive Host Cell—a host cell, including the viable protoplast thereof, which cannot grow in the presence of a given antibiotic without the presence of a DNA segment that confers resistance to the antibiotic.

Transformant—a recipient host cell, including the viable protoplast thereof, that has undergone transformation.

Transformation—the introduction of DNA into a recipient host cell, including the viable protoplast thereof, that changes the genotype of the recipient cell.

tsrR—the thiostrepton-resistance phenotype or gene conferring same.

DESCRIPTION OF THE FIGURES

The plasmid and chromosomal maps depicted in the Figures are drawn approximately to scale. The spacing of restriction sites on the map is proportional to the actual spacing of the restriction sites on the vector, but actual restriction site distances may vary somewhat from calculated distances. The tylosin biosynthetic genes of the invention, although linked, are scattered across an ~9.8 kb segment of DNA. Restriction site mapping data exists only for a few regions of the tylosin biosynthetic gene-containing DNA fragment. The maps do not necessarily provide an exhaustive listing of all the restriction sites of a given restriction enzyme.

DETAILED DESCRIPTION OF THE INVENTION

Figure 1:
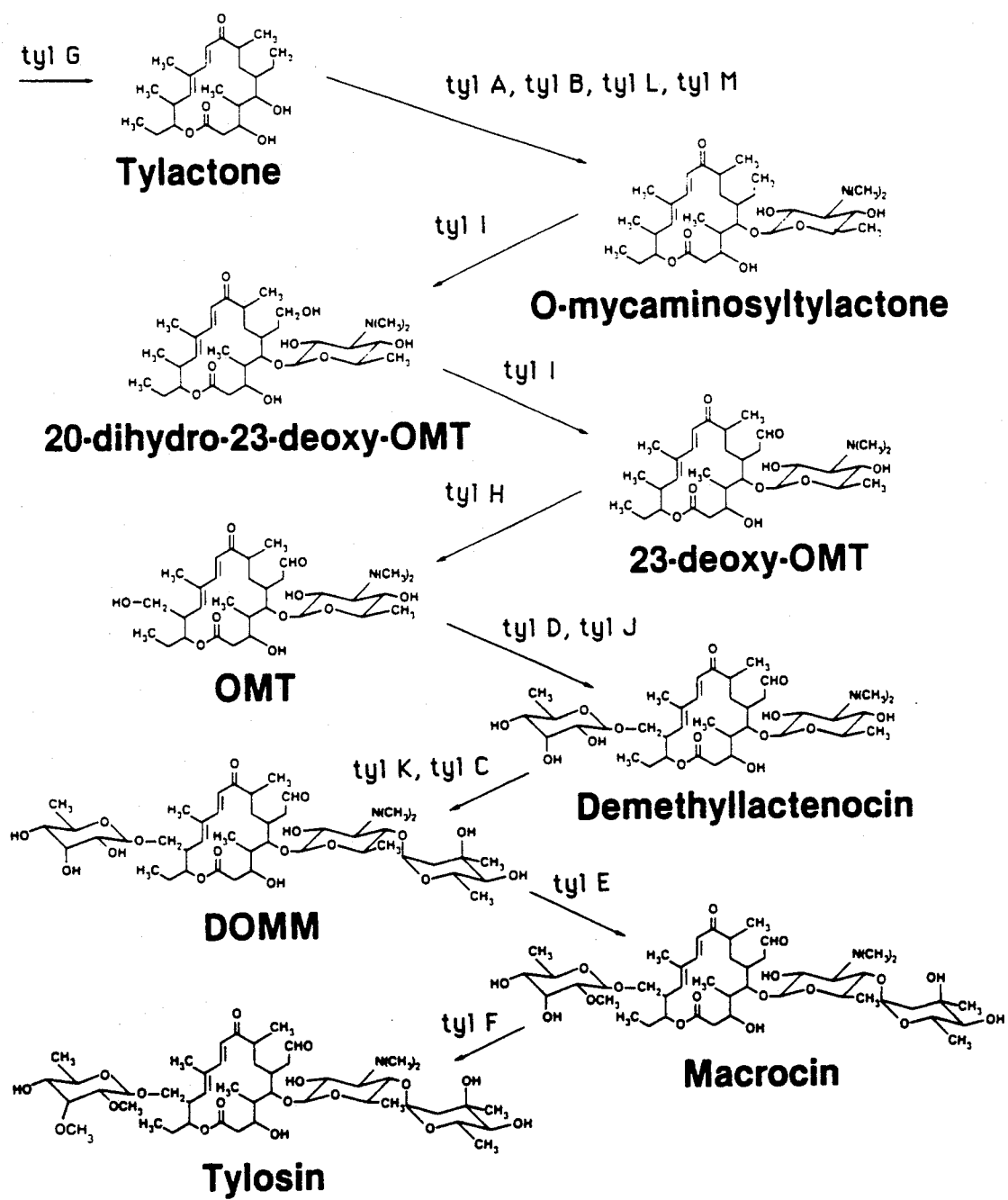
FIG. 1—The Tylosin Biosynthetic Pathway.

The invention comprises related antibiotic biosynthetic genes, recombinant DNA cloning vectors, and antibiotic or antibiotic precursor-producing microorganisms transformed with the aforementioned genes and vectors. In particular, the invention provides the previously unknown tylA, tylB, tylG and tylI biosynthetic genes, vectors containing these genes and the polypeptide activity expressed by these genes. Further, the invention relates to the polypeptide products encoded by the individual antibiotic biosynthetic genes of the invention.

The present invention also provides a method for increasing the antibiotic-producing ability of an antibiotic-producing microorganism, said method comprising 1) transforming with a recombinant DNA cloning vector or portion thereof a microorganism that produces an antibiotic or antibiotic precursor by means of an antibiotic biosynthetic pathway, said vector or portion thereof comprising an antibiotic biosynthetic gene of the invention that codes for the expression of an enzyme or other gene product that is rate limiting in said antibiotic biosynthetic pathway, and 2) culturing said microorganism transformed with said vector under conditions suitable for cell growth, expression of said antibiotic biosynthetic gene, and production of said antibiotic or antibiotic precursor.

The biosynthetic genes of the invention, when inserted into a stably maintained vector in a host cell, preferably a Streptomycete host cell, can produce, upon expression, a higher level of gene product. This in turn may accelerate the steps in the tylosin biosynthetic pathway affected by the resulting activity, ultimately resulting in increased yields of the final antibiotic product.

In addition, the introduction of the biosynthetic genes of the invention into other macrolide or similar antibiotic producing organisms can be used to produce novel hybrid antibiotics. For example, as noted earlier, tylB encodes an activity responsible for the biosynthesis or mycaminose. When introduced into, for example, an erythromycin producer, the gene could produce mycaminosyl derivatives of erythromycin. Tables I and II are non-exhaustive lists of macrolide, or similar antibiotic-producing organisms, in which the biosynthetic genes of the invention may be useful.

TABLE I

| Macrolide, Lincosamide, and Streptogramin Antibiotic-Producing Organisms | |
|---|---|
| Organism | Antibiotic |
| *Micromonospora* | |
| rosaria | rosaramicin |
| *Streptomyces* | |
| albireticuli | carbomycin |
| albogriseolus | mikonomycin |
| albus | albomycetin |
| albus var. coilmyceticus | coleimycin |
| ambofaciens | spiramycin and foromacidin D |
| antibioticus | oleandomycin |
| avermitilis | avermectins |
| bikiniensis | chalcomycin |
| bruneogriseus | albocycline |
| caelestis | M188 and celesticetin |
| cinerochromogenes | cineromycin B |
| cirratus | cirramycin |
| deltae | deltamycins |

TABLE I-continued

Macrolide, Lincosamide, and Streptogramin Antibiotic-Producing Organisms

| Organism | Antibiotic |
| --- | --- |
| djakartensis | niddamycin |
| erythreus | erythromycins |
| eurocidicus | methymycin |
| eurythermus | angolamycin |
| fasciculus | amaromycin |
| felleus | argomycin and picromycin |
| fimbriatus | amaromycin |
| flavochromogenes | amaromycin and shincomycins |
| fradiae | tylosin |
| fungicidicus | NA-181 |
| fungicidicus var. espinomyceticus | espinomycins |
| furdicidicus | mydecamycin |
| goshikiensis | bandamycin |
| griseofaciens | PA133A and B |
| griseoflavus | acumycin |
| griseofuscus | bundlin |
| griseolus | griseomycin |
| griseospiralis | relomycin |
| griseus | borrelidin |
| griseus ssp. sulphurus | bafilomycins |
| halstedi | carbomycin and leucanicidin |
| hygroscopicus | tylosin |
| hygroscopicus subsp. aureolacrimosus | milbemycins |
| kitastoensis | leucomycin $A_3$ and josamycin |
| lavendulae | aldgamycin |
| lincolnensis | lincomycin |
| loidensis | vernamycin A and B |
| macrosporeus | carbomycin |
| maizeus | ingramycin |
| mycarofaciens | acetyl-leukomycin, and espinomycin |
| narbonensis | josamycin and narbomycin |
| narbonensis var. josamyceticus | leucomycin $A_3$ and josamycin |
| olivochromogenes | oleandomycin |
| platensis | platenomycin |
| rimosus | tylosin and neutramycin |
| rochei | lankacidin and borrelidin |
| rochei var. volubilis | T2636 |
| roseochromogenes | albocycline |
| roseocitreus | albocycline |
| spinichromogenes var. suragaoensis | kujimycins |
| tendae | carbomycin |
| thermotolerans | carbomycin |
| venezuelae | methymycins |
| violaceoniger | lankacidins and lankamycin |

TABLE II

Miscellaneous Antibiotic-Producing Streptomyces

| Antibiotic Type | Streptomyces Species | Antibiotic |
| --- | --- | --- |
| amino acid analogues | sp. | cycloserine |
| cyclopentane ring-containing | coelicolor | methylenomycin A |
|  | erythrochromogenes | sarkomycin |
|  | kasugaensis | aureothricin and thiolutin |
|  | violaceoruber | methylenomycin A |
| nitro-containing | venezuelae | chloramphenicol |
| polyenes | griseus | candicidin |
|  | nodosus | amphotericin B |
|  | noursei | nystatin |
| tetracyclines | aureofaciens | tetracycline, chlortetracycline, demethyltetracycline, and demethylchlortetracycline |
|  | rimosus | oxytetracycline |

Several *Streptomyces fradiae* strains are described herein that have mutant tylosin biosynthetic genes and thus make much less or ny tylosin compared to the strain from which they were derived. Table III provides a brief description of these mutant strains.

TABLE III

Streptomyces fradiae Mutants Defective in Tylosin Biosynthesis

| Strain Designation | Mutant Gene | ATCC* or NRRL Accession No. | Deposit Date |
| --- | --- | --- | --- |
| GS5 | tylG | NRRL 18415 | Sept. 14, 1988 |
| GS14 (A252.5) | tylA | NRRL 12188 | June 13, 1980 |
| GS50 (A252.6) | tylB | NRRL 12201 | July 10, 1980 |
| GS77 (A252.8) | tylI, tylD | ATCC 31733 | Oct. 16, 1980 |

Alternate designations
*ATCC is the American Type Culture Collection, 12301 Parklawn Drive, Rockville, MD 20852, and NRRL is the Agricultural Research Culture Collection of the Northern Regional Research Laboratory, Peoria, IL 61604.

These strains were deposited and are maintained in the permanent culture collections of the noted depositories in accordance with the terms of the Budapest Treaty. NRRL 12188, NRRL 12201, and ATCC 31733 are available to the public under the noted accession numbers. All restrictions on the availability of NRRL 18415 will be irrevocably removed upon issuance or publication of the present patent application or its foreign equivalents.

*Streptomyces fradiae* ATCC 31733 and the products produced by this tylI blocked mutant are described in detail in U.S. Pat. No. 4,304,856 (Dec. 8, 1981), incorporated herein by reference. *Streptomyces fradiae* NRRL 12188 and the product produced by this tylA blocked mutant are described in detail in U.S. Pat. No. 4,366,247 (Dec. 28, 1982), incorporated herein by reference. Further, *Streptomyces fradiae* NRRL 12201 and the products produced by this tylB mutant are described in U.S. Pat. No. 4,440,857 (Apr. 3, 1984), also incorporated herein by reference.

These mutant strains help to verify the presence or absence of the gene sequences of the invention. In particular, using complementation or hybridization studies familiar to those skilled in the art, one can determine whether a given gene sequence of the invention is present on a particular gene fragment. For example, transformation of a *Streptomyces fradiae* mutant deficient for a particular gene product with an expression vector supplying upon expression the missing polypeptide product should restore normal, or near normal, production of the final end product, for example, tylosin. By way of illustration, one can transform *Streptomyces fradiae* GS14 (tylA deficient, NRRL 12188) with a gene believed to comprise the tylA DNA sequence. Upon culturing the transformed organism under conditions suitable for cell growth and expression of the transformed gene, GS14 should then produce at least near normal quantities of tylosin, the final product in the biosynthetic pathway. Likewise, similar analyses can be performed using mutant strains deficient in a single tylG, tylB or tylI product if one wants to determine whether the sequence in questions encodes the tylG, tylB, or tylI products, respectively. If the sequence fails to supply the missing activity, the biosynthetic pathway will be "clocked" at the step at which the mutant fails to produce the questioned activity. In the specific case of GS77, a second mutation in the tylD gene exists. Thus, to find tylosin as the final product, the tylD product also must be supplied. The tylD gene is described in European Patent Publication, EPA 0 238 323 (Published Sep. 23, 1987). Under usual circumstances, however, if the sequence in question fails to provide the missing activity and if the host cell contains, for example, only a single mutation, for example, in the tylI gene, upon transformation with the expression vector, O-mycaminosyl-tylactone, as well as the shunt product, 4′-O-mycarosyl-O-mycaminosyltylactone, would tend to accumulate rather than the desired tylosin final product.

For the purposes noted above, one skilled in the art will appreciate that the specific mutants noted can be substituted with other mutant strains. In addition, one skilled in the art is familiar with the methods for producing alternate mutant strains. Any mutagenic method, for example, treatment with ultraviolet light, x-rays, gamma rays or N-methyl-N'-nitro-N-nitrosoguanidine, is satisfactory for preparing alternate mutant strains. As long as one knows for what gene the mutant is deficient, the resulting organism can be used to determine the presence or absence of the desired gene in the manner described above.

The vectors of the invention provide a means for increasing the efficiency of the tylosin biosynthetic pathway by not only providing a non-defective gene but also by increasing the copy number of the tylA, tylB, tylI and tylG biosynthetic genes in mutant or non-mutant strains and by increasing the intracellular amount of the products specified by these genes. The concentration of available tylG gene product, for example, will thus be increased, resulting in an elevated amount of the activity responsible for synthesizing tylactone, followed by the conversion of tylactone to O-mycaminosyltylactone to tylosin in the tylosin biosynthetic pathway (See FIG. 1). Similarly, the concentration of available tylA, tylB or tylI gene product can be increased, resulting in the production of elevated amounts of the polypeptide activity necessary for driving the corresponding conversion of the tylosin precursors (noted in FIG. 1).

In addition, having these genes localized, one skilled in the art will appreciate that it is possible to directly manipulated the antibiotic biosynthetic genes and encoded products. Thus, one skilled in the art will be able to modify, for example, by mutation, deletion, or direct chemical modification or synthesis of the natural gene sequence so as to obtain DNA sequences encoding the same, improved or modified activity. Such modified activities, for example, may produce broader or more specific substrate specificity of the encoded activity and may allow for the production of novel antibiotics in the manner described previously. Likewise, one skilled in the art can modify the biosynthetic genes in a manner which allows for greater throughput or efficiency of the activity even though functionally the modified activity is equivalent to that encoded by the natural sequence. Further, for those activities related to regulatory functioning of the biosynthetic pathway, one skilled in the art is familiar with modification techniques which would allow for greater control over later steps in the biosynthetic pathway. Thus, one could manipulated the pathway and the products produced in any manner desired. These functionally equivalent modified or synthesized genes and gene products, therefore, are meant to be encompassed by the terms "gene", "DNA sequence", or the "polypeptide", "amino acid sequence", "activity" or "product" encoded by such genes.

A schematic representation of the tylosin biosynthetic pathway is presented in FIG. 1; each arrow in FIG. 1 represents a conversion step in the biosynthesis of tylosin that is catalyzed by one or more tylosin biosynthetic gene products, as indicated by the gene name(s) located above each arrow. For example, tylG is involved in the synthesis of tylactone, tylA is involved in the attachment or biosynthesis of tylosin sugars whereas tylB is related to the attachment or synthesis, specifically, of mycaminose. Further, tylI is required for the oxidation at the C-20 position. Each genotypic designation may represent a class of genes that contribute to the same phenotype.

A number of vectors are used to exemplify the present invention. These vectors comprise one or more tylosin biosynthetic genes and can be obtained from the Northern Regional Research Laboratories (NRRL), Peoria, Ill. 61604. Table IV provides a brief description of each of the plasmids containing the tylosin biosynthetic genes of the present invention.

TABLE IV

Figure 5:
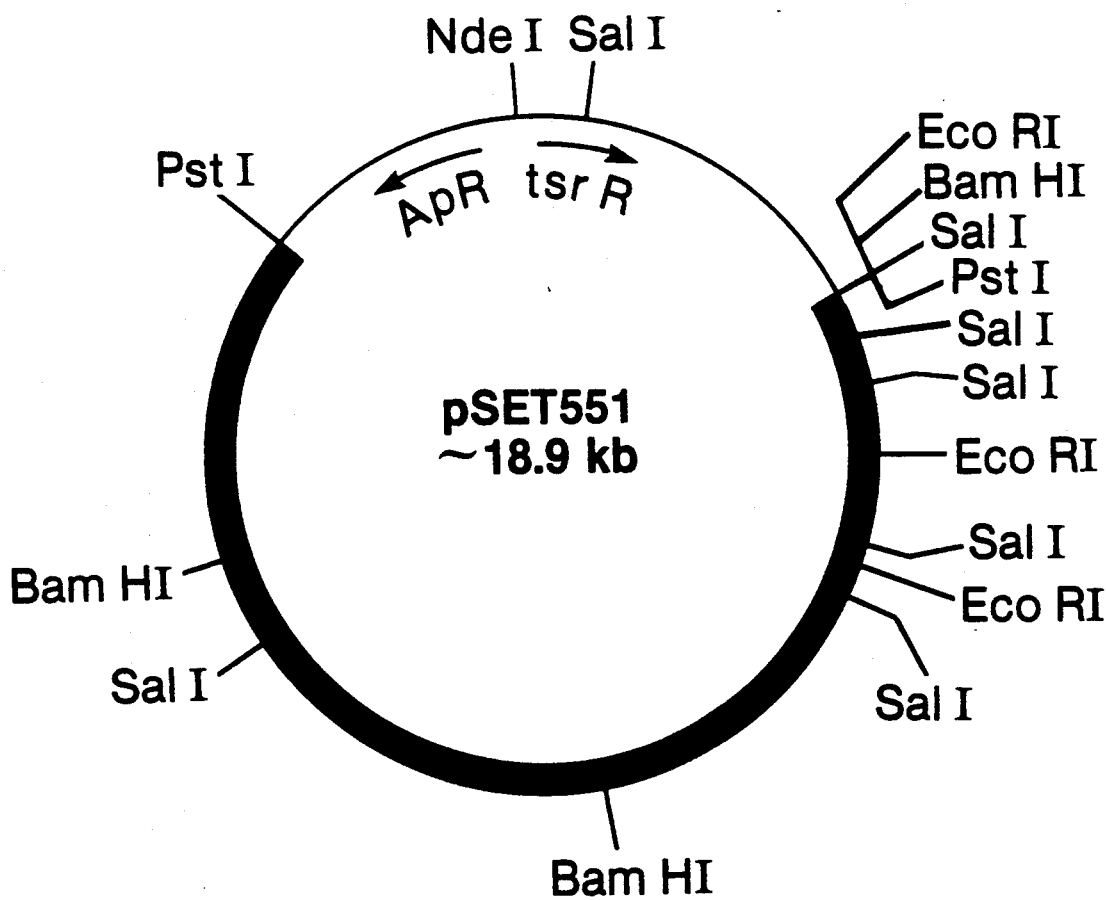
FIG. 5—Restriction Site and Function Map of Plasmid pSET551.
Figure 6:
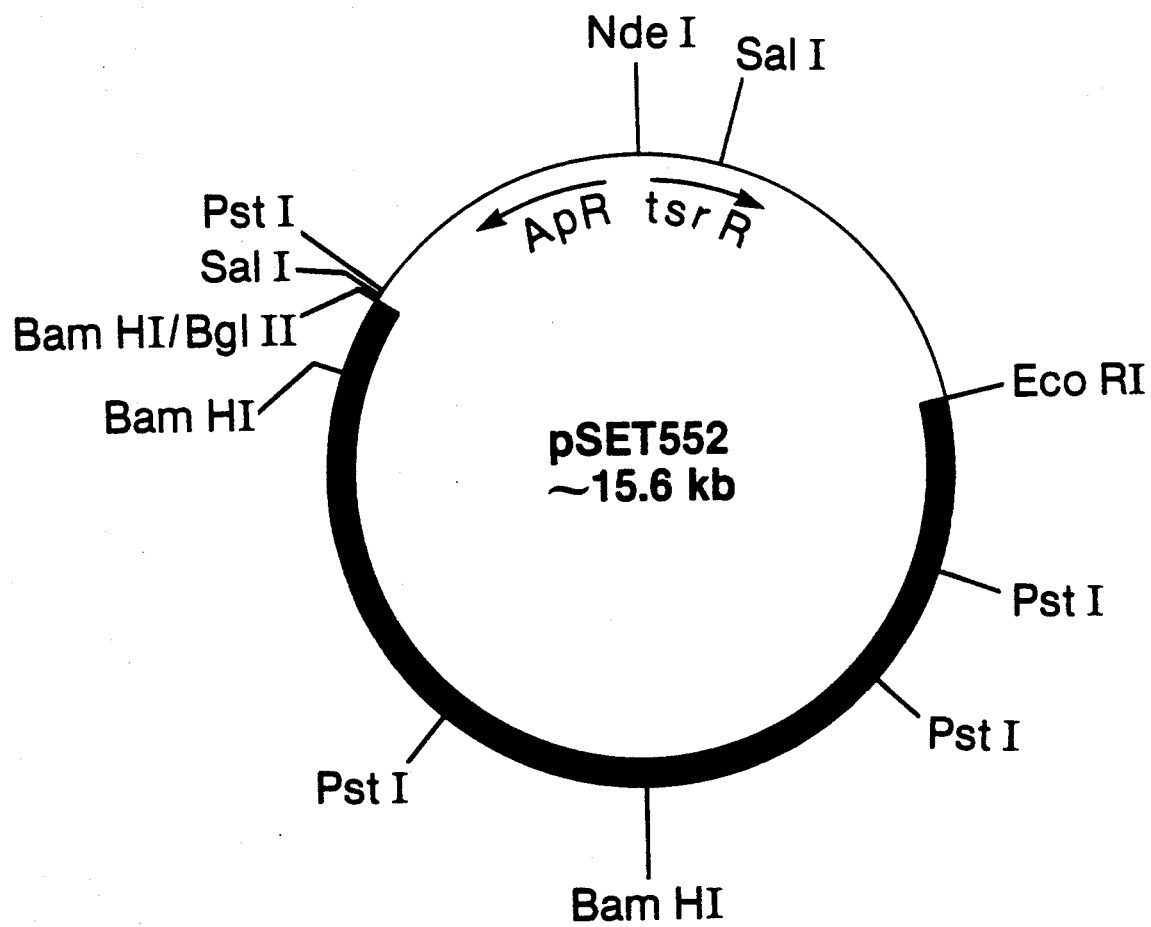
FIG. 6—Restriction Site and Function Map of Plasmid pSET552.
Figure 7:
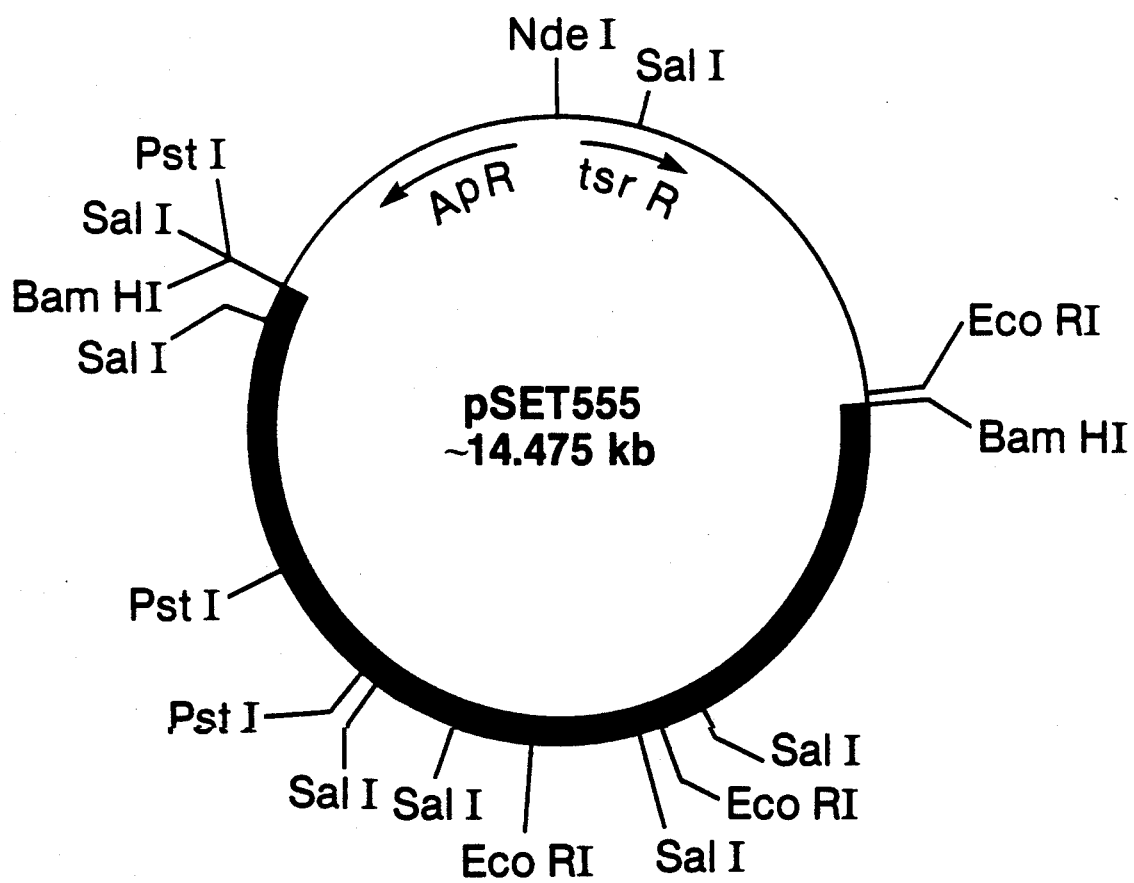
FIG. 7—Restriction Site and Function Map of Plasmid pSET55.
Figure 8:
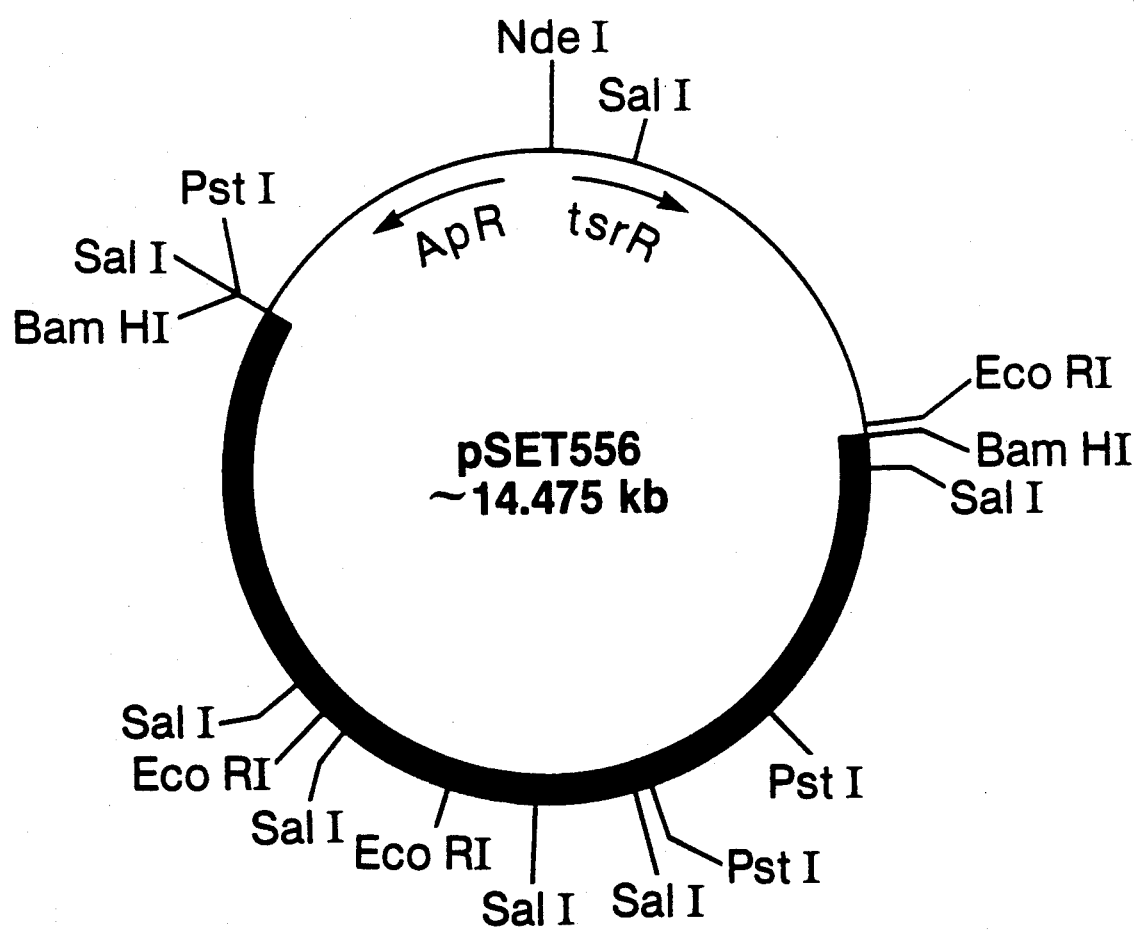
FIG. 8—Restriction Site and Function Map of Plasmid pSET556.

| Plasmids Comprising Tylosin Biosynthetic Genes | | | |
|---|---|---|---|
| Host/Designation | Tylosin Gene(s) | NRRL Accession No. | Map |
| E. coli K12 DH5α/pSET551 | G, I | B-18411 | FIG. 5 |
| E. coli K12 DH5α/pSET552 | I, A, B | B-18412 | FIG. 6 |
| E. coli K12 DH5α/pSET555 | G, I, A, B | B-18413 | FIG. 7 |
| E. coli K12 DH5α/pSET556 | G, I, A, B | B-18414 | FIG. 8 |

The tylA, tylB, tylG and tylI genes provided by the present invention are located within a previously unknown tylosin biosynthetic gene cluster approximately 30 kb rightward of the previously described Streptomyces fradiae tylosin biosynthetic gene cluster (See e.g. published European Application, EP A 0 238 323 (Sep. 23, 1987) and Fishman, et al., Proc. Natl. Acad. Sci. U.S.A., 84, 8248 (1987)). This cluster is bounded on the right by a tylosin resistance gene, tlrC, and on the left by repeating sequences, RS$_2$ and RS$_1$. See FIG. 9 in this regard.

These genes were obtained from a cosmid library of Streptomyces fradiae DNA inserted into cosmid vector pKC462A. Cosmid vector pKC462A has been transformed into host cell E. coli K12 SF-8 and deposited in the NRRL. A sample of this host containing this cosmid can be obtained from the NRRL under the accession number B-15973.

Plasmid pKC668 contains a fragment of Streptomyces ambofaciens DNA which complements tylA and tylB mutant strains such as GS14 and GS50. This plasmid served as a hybridization probe to identify homologous Streptomyces fradiae DNA present on the cosmids obtained from the Streptomyces fradiae cosmid library described above.

Figure 2:
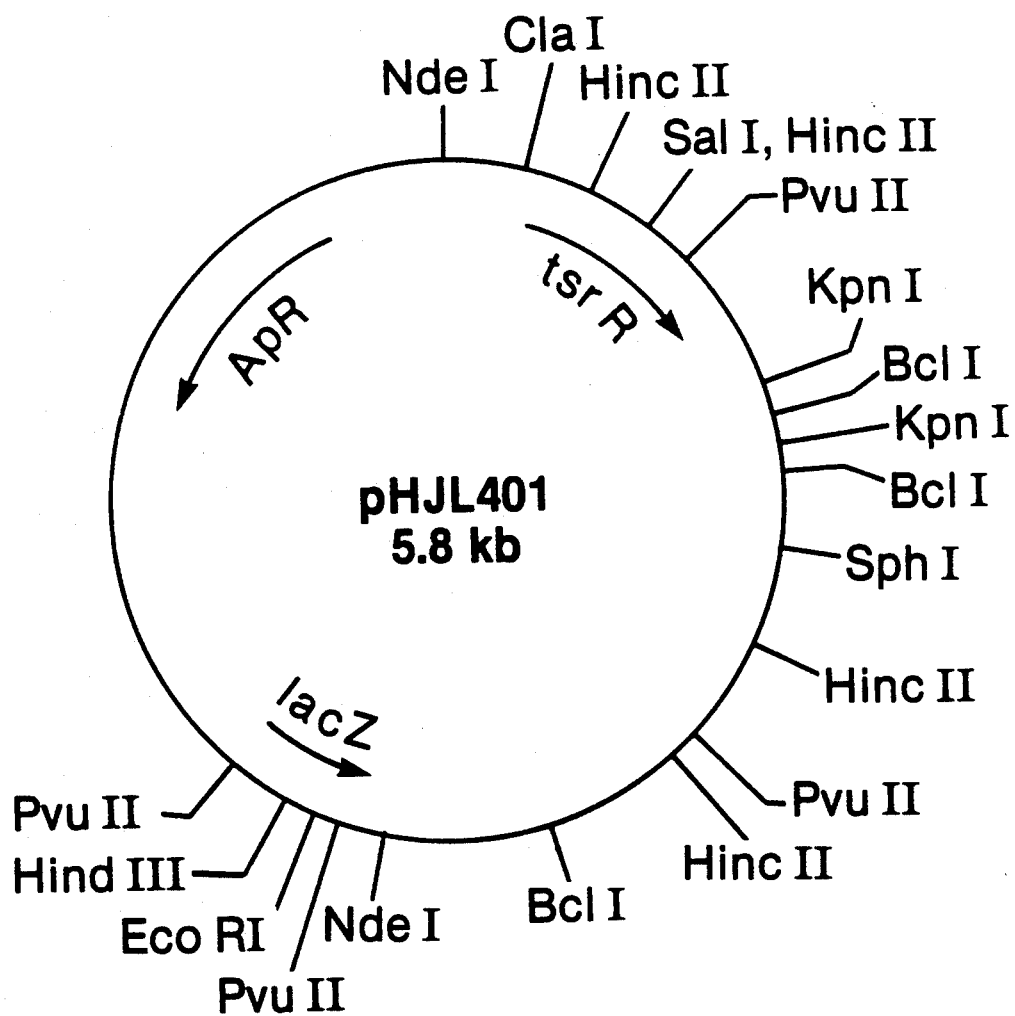
FIG. 2—Restriction Site and Function Map of Plasmid pHJL401.
Figure 3:
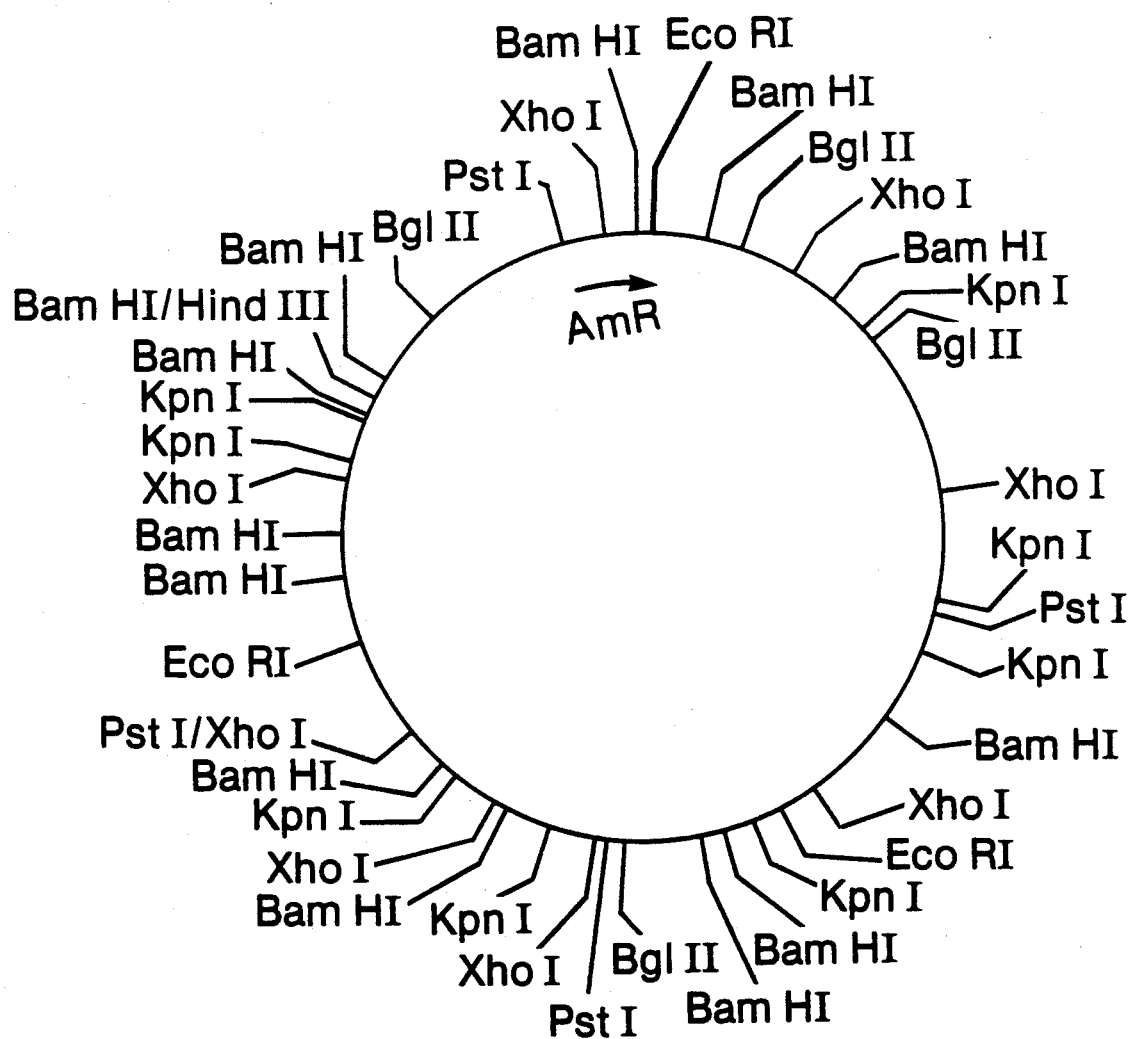
FIG. 3—Restriction Site and Function Map of Plasmid pKC644.

Plasmid pKC668 is generated by digesting cosmid pKC644 with restriction enzyme EcoRI, isolating the resulting ~10 kb EcoRI restriction fragment, and ligating the fragment with EcoRI-digested plasmid pHJL401 (FIG. 2). Plasmid pHJL401 is available from the NRRL under the accession number NRRL B-18217 and is described in Larson and Hershberger, 1986, Plasmid 15:199-209. Cosmid pKC644 is deposited in *E. coli* K12 DK22 in the Northern Regional Research Center (NRRL), Peoria, Ill. under the accession number NRRL B-18238. The restriction map of pKC644 is shown in FIG. 3. The ~10 kb EcoRI fragment, when ligated to digested pHJL401, results in two plasmids differing only in the orientation of the inserted DNA. These plasmids are designated pKC668A and pKC668. The orientation of the ~10 kb EcoRI restriction fragment can be determined by restriction enzyme analysis familiar to one skilled in the art.

Other fragments, including overlapping restriction fragments, from the *S. fradiae* cosmid library were used to determine by complementation the presence of of the tylG, tylI, tylA and tylB gene sequences. For example one cosmid vector designated AUD 8-2 contains an ~13 mb PstI fragment which, when subcloned into pHJL401, complements tylosin mutant strains GS5 and GS77. Likewise, cosmid vector tlrC 8-6 contains an ~8.6 BamHI fragment which when subcloned into pHJL401, is found to complement upon transformation GS5, GS14, GS50 and GS77 thereby confirming the presence of the tylG, tylA, tylB and tylI genes, respectively. Similarly, an ~9.8 kb EcoRI-BglII fragment of plasmid tlrC 4-3.24, when inserted in pHJL401, is found to complement the tylI, tylA and tylB mutants previously described.

As noted, plasmid pHJL401 (NRRL B-18217) is a shuttle vector containing a replicon specifying a moderate plasmid copy number in streptomycetes as well as being able to replicate in *E. coli*. Plasmid pHJL401 contains a polylinker sequence located between the HindIII and EcoRI sites in the lacZ region of the plasmid (FIG. 2). This polylinker provides unique insertion sites for HindIII, PstI, XbaI, BamHI, XmaI, SmaI, SacI and EcoRI. These sites are useful for "sticky-end" ligations for the tylosin biosynthetic gene fragments noted above.

In particular, the ~13 kb PstI fragment of AUD 8-2, when inserted into PstI digested pHJL401 produces plasmid pSET551, (NRRL B-18411), the restriction map of which is shown in FIG. 5. Likewise, insertion of the ~9.8 kb EcoRI-BglII fragment of tlrC 4-3.24 into a EcoRI-BamHI digested pHJL401 results in plasmid pSET552 (NRRL B-18412), the restriction map of which is shown in FIG. 6. Also, the ~8.6 kb BamHI fragment of tlrC 8-6 when inserted into BamHI digested pHJL401 results in plasmids pSET555 (NRRL B-18413) and pSET556 (NRRL B-18414), the restriction maps of which are shown in FIGS. 7 and 8, respectively.

Figure 9:
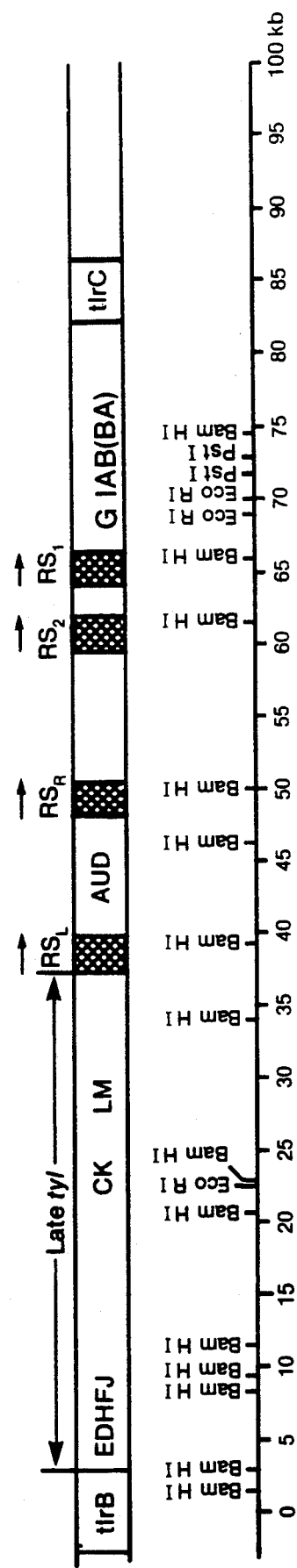
FIG. 9—Genomic Map of S. fradiae Tylosin Biosynthetic Genes.

Further complementation with overlapping sequences and restriction site analyses would indicate that the tylG biosynthetic gene is comprised on an ~4.2 kb BamHI-EcoRI fragment of pSET555, pSET551 or pSET556. In addition, the tylI gene is contained on an ~1.4 kb EcoRI-PstI fragment of pSET555, pSET556, pSET551 or pSET552. Although the orientations of the tylA and tylB biosynthetic genes are unclear, as shown in FIG. 9, these genes can be isolated on an ~6.2 kb EcoRI-PstI restriction fragment of pSET552. As one skilled in the art will appreciate, appropriate routine restriction enzyme treatment of the indicated vectors will produce fragments containing the biosynthetic genes of the invention.

The tyl gene-containing fragments noted above can be ligated into other vectors to make other useful vectors. Such other vectors may include, for example, those vectors disclosed in U.S. Pat. Nos. 4,468,462; 4,513,086; 4,416,994; 4,503,155; and 4,513,185; and also plasmids pIJ101, pIJ350, pIJ702 (ATCC 39155), SCP2* (NRRL 15041), pOJ160 (NRRL B-18088), pHJL192, pHJL197, pHJL198, pHJL210, pHJL211, pHJL400, pHJL302, pIJ922, pIJ903, pIJ941, pIJ940, and pIJ916. These vectors replicate and are stably maintained in *Stretomyces fradiae* and other tylosin-producing strains and, therefore, are useful for cloning the present antibiotic biosynthetic genes.

Likewise, as discussed below, if integration of the vector into the genome is desired, a variety of techniques are available. Particularly useful integrative vectors may include, for example, derivatives of φC31 (Chater, et al., *Gene*, 26, 67 (1983); Methods of Microbiology, Ch. 4, (1981)). One such vector is phasmid pKC331 which can be obtained from *E. coli* K12 BE447/pKC331 (NRRL B-15828). Likewise, other integrative vectors comprise vectors such as the *S. coelicolor* minicircle (for example, pIJ4210) [See, for example, Lydiate, et al., Proc. of the 5th Intl. Symposium on the Genetics of Industrial Microorganisms pp. 49-56 (1986); Lydiate, et al., *Mol. Gen., Genet.* 203, 79 (1986)] or derivatives of pSAM2 See, for example, Pernodet, et al., *Mol. Gen. Genet.* 198, 35 (1984); Simonet, et al., *Gene* 59 137 (1987).

Illustrative host strains for the vectors noted above may include, for example, *S. fradiae, S. fradiae* GS5, *S. fradiae* GS14, *S. fradiae* GS50, *S. fradiae* GS77, *S. coelicolor, S. lividans, S. thermotolerans,* and *S. ambofaciens.* Preferably integrative vectors derived from φC31 or pSAM2 are transformed into host strains *S. ambofaciens, S. coelicolor, S. lividans* or *S. fradiae.* The preferred Streptomyces host strains for the pHJL401 derived vectors are *S. fradiae* GS5, *S. fradiae* GS14, *S. fradiae* GS50 or *S. fradiae* GS77. Vectors derived from the *S. coelicolor* minicircle are preferably transformed into host strains *S. lividans, S. coelicolor,* or *S. fradiae.* Other representative Streptomyces host strains may include, for example, *S. rimosus* and *S. hygroscopicus.*

*Streptomyces hygroscopicus* and *S. rimosus* are well known, having been deposited at the American Type Culture Collection (ATCC), Rockville, Md. 20852. A number of strains of *S. hygroscopicus* can be obtained under the accession numbers ATCC 27438, ATCC 21449, ATCC 15484, ATCC 19040, and ATCC 15420, and *s. rimosus* can be obtained under the accession number ATCC 10970. *Streptomyces fradiae* is also an especially well known microorganism and several strains are available, on an unrestricted basis, from the Northern Regional Research Laboratory (NRRL), Peoria, Ill. 61604 and the ATCC under the accession numbers NRRL 2702, NRRL 2703, and ATCC 19609. *Streptomyces ambofaciens,* also well-known, is available from the ATCC under the accession numbers ATCC 15154 and ATCC 23877, or from the NRRL under the accession number NRRL 2420. Likewise, strains of *S. coelicolor* are available from the ATCC under the accession numbers ATCC 3355, ATCC 10147, ATCC 13405, ATCC 19832 or ATCC 21666. *S. lividans* is available from the ATCC under the accession number ATCC 19844. Finally, *S. thermotolerans* is available from the ATCC under the accession number ATCC 11416.

As noted, the vectors of the present invention can increase the antibiotic-producing ability of an antibiotic-producing organism by providing higher levels, as compared to an untransformed organism, of an enzyme or other gene product or activity that is rate-limiting in an antibiotic biosynthetic pathway. However, plasmid maintenance in an antibiotic-producing host cell sometimes requires significant expenditures of the cell's energy, energy that might otherwise be used to produce antibiotic. Thus, certain microorganisms transformed with autonomously replicating vectors actually show a decrease in antibiotic-producing ability, even though the same vectors can increase the antibiotic-producing ability of other organisms.

The synthesis of antibiotics is also believed to be a dispensable function in antibiotic-producing organisms, for mutants blocked in the biosynthesis of antibiotics are viable and grow as well as the antibiotic-producing parent. Wild-type strains produce a relatively small amount of antibiotic, which is apparently adequate to provide the organism with a selective advantage.

The development of industrial antibiotic producing strains from natural isolates involves many cycles of mutation and selection for higher antibiotic production. Because the synthesis of antibiotics drains primary metabolites and cellular energy away from growth and maintenance functions, selection for higher antibiotic production frequency occurs at the expense of the vitality of the organism. Thus, the generation of high antibiotic-producing strains involves finely balancing the cells nutritional and energy resources between growth-maintenance functions and antibiotic production. As a consequence of this fine-tuning, high-yielding production strains tend to be extremely sensitive to factors that affect cellular physiology. For example, introduction of autonomously-replicating vectors, notably multicopy plasmids, sometimes tends to decrease the antibiotic-producing ability of an organism that normally produces antibiotics at high levels. The mechanism of this inhibition is not clear, but it is through to occur at an early step in the biosynthesis of the antibiotic, because measurable levels of antibiotic precursors do not accumulate under these conditions. In addition, autonomously replicating vectors may drain pools of precursors for DNA or RNA synthesis or, in high copy number, may titrate DNA binding proteins, such as RNA polymerase, DNA polymerase, polymerase activators, or repressors of gene expression. Another frequent limitation of autonomously replicating vectors is spontaneous loss. Spontaneous loss is especially problematical when the vector reduces growth rate, as frequently occurs. Selection for a resistance marker on the plasmid can ensure the growth of homogeneous, plasmid-containing populations but can also disrupt the physiological balance of an antibiotic fermentation. Selection for unstable plasmids operates by killing or inhibiting the bacteria that lose the plasmid and can result in a reduced growth rate.

The negative effect, sometimes observed, of autonomously replicating vectors on the antibiotic-producing ability of a microorganism is greatest in high-producing strains that are delicately balanced with respect to growth-maintenance functions and antibiotic production. The problem of the negative effect of autonomous plasmid replication on high-producing strains can be overcome by methods of culturing the transformed host cell to facilitate identification of transformed cells containing integrated plasmid and, in addition, by providing vectors with features that also facilitate detection of integration. Selecting a culturing procedure that results in integration is important in improving the antibiotic-producing ability of highly selected and conventionally improved antibiotic-producing organisms. Organisms or strains that have a low antibiotic-producing ability can be improved by transformation via either integration or autonomous vector replication. As those skilled in the art of fermentation technology will appreciate, the greatest improvement in antibiotic-producing ability is shown when the present invention is applied to low antibiotic-producing strains.

Therefore, if desired, integration of plasmid DNA is readily accomplished by transforming, according to standard transformation procedures, with a vector which is either segregationally unstable or which is unable to replicate in the strain, a given antibiotic-producing strain or mutant thereof, selecting or otherwise identifying the transformants, and then culturing the cells under conditions that do not require the presence of plasmid DNA sequences for the host cell to grow and replicate. After several generations under non-selective conditions, certain cells will no longer contain free plasmid DNA. By selecting for or otherwise identifying plasmid DNA sequences present in the host cell, one can identify host cells in which the plasmid DNA has integrated into the chromosomal (genomic) DNA of the cell. This culturing technique to obtain integration of vector DNA is especially useful when used in conjunction with a vector that is inherently unstable in the transformed host cell, so that culturing without selective pressure to maintain the vector generates segregants that are free of the plasmid. Bibb et al., 1980, Nature 384:526–531, described a DNA sequence needed for stable inheritance of a vector, and a variety of vectors have been constructed that lack this stability sequence.

For instance, cloning vector pHJL401 (NRRL B-18217), which was used to construct the plasmids of the invention, lacks this stability sequence. As used, "unstable" refers to plasmids that are lost at high frequency by transformed cells only when those cells are cultured in the absence of selective pressure for plasmid maintenance. Normally plasmids such as pHJL401 are quite stable when selective pressure is applied to the transformed host cell. When host cells transformed with stable vectors are cultured in the absence of selective pressure, the vector is not lost with the high frequency observed with unstable vectors, and identification of integrants is made difficult by the great number of cells that still contain autonomously replicating plasmid even after growth under nonselective conditions. Selection for integrants is more fully described below. Once the vector DNA has integrated into the chromosomal DNA of the host cell, one observes the maximum increase in antibiotic-producing ability for that host cell, because inhibition by autonomously replicating plasmids no longer occurs.

Integration of vectors containing cloned genes into the genome of the producing organism can be achieved in a number of ways. One way is to use a lysogenic bacteriophage or other phage vector that can integrate into the genome of the host strain. Another approach is to use a plasmid vector carrying the cloned genes and to screen for integration of the recombinant plasmid into the host genome by a single recombination event between the cloned sequence and the homologous chromosomal sequence. Integration frequency of a vector can be dramatically increased by adding DNA homologous to the genomic DNA of the host cell to the vector. As used, "integration" refers both to a single recombination event, known as Campbell-type recombination, and also to a double-crossover event, which results in exchange of genetic information between the vector and the chromosome. With double-crossover recombination, only a portion of the vector integrates into the chromosomal DNA.

For example, a plasmid carrying cloned tylosin biosynthetic genes (tyl) could integrate into the *Streptomyces fradiae* genome by a single crossover between the tyl genes on the plasmid and the homologous tyl genes in the genome. Another option would be to put a non-tyl *S. fradiae* DNA sequence on the plasmid in addition to the cloned tyl genes and to screen for integration at the locus corresponding to the non-tyl sequence. The latter approach avoids the possible mutagenic effects of integration into the tyl sequences, but if double-crossover recombination is desired, the vector should comprise the antibiotic biosynthetic genes flanked by separate sequences of homologous DNA.

To avoid the potentially adverse effects, however remote, of a recombinant plasmid (either autonomously replicating or integrated) on tylosin production, one can make use of the ability of *Streptomyces fradiae* to take up tylosin precursors from the culture medium and convert them to tylosin.

Thus, one can develop specific strains of *S. fradiae* containing multiple copies of the present biosynthetic genes and high enzyme levels to act as converters of accumulated precursors to tylosin. These converter strains can be used in several different ways: (1) the converter strain can be co-inoculated into the fermentor with the normal production strain at a low ratio of converter:producer; (2) the converter strain can be introduced into a production fermentation culture late in the cycle to convert intermediates; (3) the converter strain can be kept in a separate "reactor", to which the fermentation production broth from the producer strain would be added; or (4) the converter strain can be immobilized on a column, and fermentation broth from the producer strain passed through. Those skilled in the art will recognize that having separate production and converting populations eliminates the adverse effects that recombinant plasmids sometimes have on antibiotic production in high antibiotic-producing strains.

Separate populations also eliminate vector stability problems, because the converting strains can be grown in small vessels in which antibiotic selection or some other selection means for maintenance of the plasmid can be carefully regulated and controlled. In essence, the converting strain is a source of enzymes, and the production of these enzymes at high level can be approached in much the same way as production of proteins from recombinant plasmids in *E. coli*.

Normally, antibiotic production is only increased when the transforming DNA comprises a gene, the expression of which enhances the activity of the rate-limiting product of the untransformed strain. Various methods for determining the rate-limiting step in the biosynthesis of an antibiotic are known in the art (Seno and Baltz, 1982, Antimicrobial Agents and Chemotherapy 21:758-763), but there is no need to identify the rate-limiting step when the entire set of antibiotic biosynthetic genes are available for introduction into the antibiotic-producing strain. If a rate-limiting enzyme is not known, the antibiotic-producing strain is transformed with the entire set of antibiotic biosynthetic genes, thus ensuring that, no matter what enzyme is rate-limiting, the transformed host cell will have higher levels of the rate-limiting enzyme than the untransformed host cell. Often, however, the rate-limiting enzyme of an antibiotic biosynthesis pathway will be known, and the genes of the invention can be used to increase the antibiotic-producing ability of the organism by transforming the organism with a vector that encodes the rate-limiting antibiotic biosynthetic enzyme.

The recombinant plasmids described in the present invention each comprise one or more antibiotic biosynthetic genes. Unless part of a polycistron, an antibiotic biosynthetic gene normally comprise: (1) a promoter that directs transcription of the gene; (2) a sequence that, when transcribed into mRNA, directs translation of the transcript ("translational activating sequence"); (3) a protein-coding sequence; and (4) a transcription terminator. Each of these elements is independently useful and can, through the techniques of recombinant DNA technology, be used to form recombinant genes of great variety. As one example, the protein-coding sequence for the tylG gene can be linked to the promoter, translation-activating sequence, and transcription-terminating sequence from a non-*Streptomyces fradiae* gene to form a recombinant gene that functions in the host from which the non-*S. fradiae* sequences were isolated. Such a novel gene could be used to produce a hybrid antibiotic if introduced into an organism that produced an antibiotic or antibiotic intermediate that is not found in the tylosin pathway but which could serve as a substrate for the novel gene product. Similarly, the promoter and other regulatory elements of the tylG gene could be linked to the coding sequence of a non-tylosin antibiotic biosynthetic gene to prepare a hybrid gene that would function in *S. fradiae*. Thus, the individual elements of each of the antibiotic biosynthetic genes on each of the plasmids of the invention comprise an important component of the present invention. That is, the promoter, translational activating sequence, protein-encoding sequence and transcription termination sequences, individually, of the biosynthetic genes of the invention, individually, comprise important aspects of the invention.

*Streptomyces fradiae* strains can be cultured in a number of ways using any of several different medium. Carbohydrate sources that are preferred in a culture medium include, for example, molasses, glucose, dextran, and glycerol, and nitrogen sources include, for example, soy flour, amino acid mixtures, and peptones. Nutrient inorganic salts are also incorporated into the medium and include the customary salts capable of yielding sodium, potassium, ammonium, calcium, phosphate, chloride, sulfate, and like ions. As is necessary for the growth and development of other microorganisms, essential trace elements are also added. Such trace elements are commonly supplied as impurities incidental to the addition of other constituents of the medium. *S. fradiae* strains are grown under aerobic culture conditions over a relative wide pH range of about 6 to 8 at temperatures ranging from about 25° to 34° C.

The following non-limiting examples further illustrate and describe the invention. The invention is not limited in scope by reason of any of the following Examples. Sources of reagents are provided merely for convenience and in no way limit the invention.

PREPARATION 1

Isolation of Cosmid pKC644

Cosmid pKC644 (FIG. 3) can be obtained from the Northern Regional Research Center (NRRL), Peoria, Ill. 61604, in *E. coli* K12 DK22 under the accession number NRRL B-18238. The cosmid pKC644 DNA is used to construct vectors useful in isolating the genes of the present invention. The lyophils of *E. coli* K12 DK22/pKC644 are plated onto L-agar plates (10 g of tryptone, 10 g of NaCl, 5 g of yeast extract, and 15 g of agar per liter) containing 200 μg/ml apramycin to obtain a single colony isolate of the strain. This colony is used to inoculate about 500 ml of L broth (L agar without agar) containing 200 μg/ml apramycin, and the resulting culture was incubated at 30° C. with aeration until the cells reach stationary phase.

Cosmid DNA is obtained from the cells in accordance with the procedure of Rao et al., 1987 in Methods in Enzymology, 153:166-198 (R. Wu and L. Grossman, eds., Academic Press, N.Y.), described below.

The cells are centrifuged at 8000 rpm for 10 minutes. After the supernatant is decanted, the cells are resuspended in 7 ml of 25% sucrose, 50 mM Tris.HCl, pH 8.0. Freshly prepared lysozyme (0.25 ml of a 5 mg/ml solution) is added to the solution, along with 0.4 ml of 0.5M EDTA (pH 8), and 0.05 ml of 5 mg/ml RNase A. The mixture is incubated for 15 minutes at 37° C. To this 0.75 ml of Triton lytic mix (150 mM Tris.HCl, pH 8.0, 3% Triton X-100 ®, 200 mM EDTA) is added, mixed, and incubated for 15 minutes on ice. If lysis is not complete, it is further incubated for about 5 minutes at 37° C. The mixture is centrifuged at 20,000 rpm for 40 minutes. The supernatant is removed and retained. A CsCl gradient (density of 1.55) is made by adding 28.65 g of CsCl to 31.2 ml of DNA solution. The gradient solution is mixed to dissolve the CsCl and transferred to large ultracentrifuge tubes. The tubes are filled with ~0.6 ml of ethidium bromide (10 mg/ml), sealed and mixed.

The gradient is centrifuged at 49,000 rpm (Beckman vTi50 rotor) for 18 hours. The lower band of plasmid DNA as visualized with long-wave UV light is collected. The ethidium bromide is removed by extracting 4 to 5 times with isoamyl alcohol saturated with CsCl. The DNA solution was dialyzed against 2 liters of TE buffer (10 mM Tris.HCl, pH 8.0, 1 mM EDTA) and after 2 hours is replaced with fresh TE. The dialyzed solution is extracted twice with phenol and twice with chloroform:isoamyl alcohol (24:1). The DNA is ethanol precipitated by adding one-tenth volume of 3M sodium acetate and 3 volumes of ethanol. The DNA is collected by centrifugation for 10 minutes at 10,000 rpm, washed with 70% ethanol and then 100% ethanol, dried and dissolved in about 250 μl of sterile TE. The concentration and purity is estimated by measuring optical density at 260 and 280 nm. A restriction site and function map of pKC644 is presented in FIG. 3 of the accompanying drawings.

PREPARATION 2

Isolation of Plasmid pHJL401

Plasmid pHJL401 (Larson and Hershberger, 1986, Plasmid 15:199-209) can be obtained from the NRRL in *E. coli* K12 JM109 under the accession number NRRL B-18217. Plasmid pHJL401 is a useful vector because it can replicate in *E. coli* or Streptomyces and it comprises two antibiotic resistance markers, ampicillin and thiostrepton. Thiostrepton is selectable only in Streptomyces; ampicillin is selectable in *E. coli*. Plasmid pHJL401 also has a polylinker multiple cloning site region in the lacZ gene. DNA inserts can thus be selected by picking white colonies when the cells are plated on Xgal. The lyophils of *E. coli* K12 JM109/pHJL401 are plated onto L-agar plates containing 100 μg/ml ampicillin, 40 μg Xgal/ml, and 40 μg IPTG/ml to obtain a single blue colony isolate of the strain. This colony is used to inoculate about 500 ml of L broth containing 100 μg/ml ampicillin, and the resulting culture is incubated at 37° C. with aeration until the cells reach stationary phase.

Plasmid DNA is obtained from the cells in substantial accordance with the procedure set forth in Procedure 1, above. A restriction site and function map of plasmid pHJL401 is presented in FIG. 2 of the accompanying drawings.

PREPARATION 3

A. Construction of Plasmid pKC668

Plasmid pKC668 contains an EcoRI restriction fragment (~10 kb) from *S. ambofaciens* which complements the mutant tylA and tylB genes in GS14 GS50. This vector is useful, therefore, in probing the *S. fradiae* genome for the tylA and tylB biosynthetic genes of the invention. The plasmid is constructed in the following manner. About 10 μg (10 μl) of plasmid pHJL401 DNA (from Preparation 2) are added to 2 μl of 10X EcoRI buffer (1M Tris-HCl, pH=7.5; 0.5M NaCl; and 50 mM MgCl$_2$), 6 μl of H$_2$O, and 2 μl (~40 units; unit definitions used throughout the examples correspond to those of New England Biolabs (NEB), 32 Tozer Road, Beverly, Mass. 01915-9990, unless otherwise indicated) of restriction enzyme EcoRI. The resulting reaction is incubated at 37° C. for two hours. The EcoRI-digested plasmid pHJL401 DNA is extracted with phenol:chloroform (1:1) and then collected by adjusting the sodium acetate (NaOAc) concentration of the aqueous phase of the reaction mixture to 0.30M, adding 2.5 volumes of ethanol, chilling the reaction mixture to −70° C., and centrifuging to pellet the precipitated DNA. The pellet of EcoRI-digested plasmid pHJL401 DNA is resuspended in 400 μl of TE buffer. About 1 μl (0.1 unit) of bacterial alkaline phosphatase (International Biotechnology, Inc. (IBI), P.O. Box 1565, New Haven, Conn. 06506) is added to the DNA solution, and the reaction is incubated at 65° C. for 1 hour. The reaction mixture is extracted with 400 μl of a 1:1 solution of phenol:chloroform and then extracted with 400 μl of chloroform. The EcoRI-digested, dephosphorylated plasmid pHJL401 DNA is collected by ethanol precipitation and centrifugation as described above, and the DNA pellet is resuspended in 10 μl of TE buffer.

About 10 μg of cosmid pKC644 (as prepared in Preparation 1) in 10 μl of TE buffer is added to 75 μl of H$_2$O, 10 μl of 10X EcoRI buffer (1M Tris-HCl, pH=7.5; 0.5M NaCl; and 50 mM MgCl$_2$), and 5 μl (~100 units) of restriction enzyme EcoRI. The resulting reaction is incubated at 37° C. for 2 hours. The reaction mixture is extracted and the DNA is collected as described above. The DNA pellet is dissolved in ~10 μl of TE buffer. The DNA is electrophoresed on a low-melting agarose gel (BioRad, 2200 Wright Ave., Richmond, Ga. 94804) in substantial accordance with the procedure in Maniatis et al., 1982, *Molecular Cloning* (Cold Spring Harbor Laboratory).

The gel is prepared by heating 100 ml of 1X TAE buffer (40 mM Tris-acetate, pH=7.5, 2 mM EDTA) containing 0.8 g of low-melting agarose until the agarose dissolves. The mixture is cooled to 37° C. poured and, then set at 4° C. Two μl of loading-buffer (0.25% bromphenol blue, 0.25% xylene cyanol, 30% glycerol in H$_2$O) is added to the DNA sample. The sample was loaded onto the gel. The gel is run at 100 V at 4° C. until the bromphenol blue dye nears the bottom of the gel. The gel was stained with 0.5 μg/ml ethidium bromide and the desired ~10 kb EcoRI band was detected by long wave UV fluorescence and excised. To the gel piece is added 5 volumes of 20 mM Tris-HCl (pH 8.0) and 1 mM EDTA. The gel is melted at 65° C. for 5 minutes. The sample is extracted with an equal volume of phenol. The sample is centrifuged, the aqueous layer recovered and reextracted, and the DNA is collected as described above.

The DNA pellet is dissolved in 40 μl of TE buffer and contains ~2 μg of the desired ~10 kb EcoRI restriction fragment of cosmid pKC644.

Figure 4:
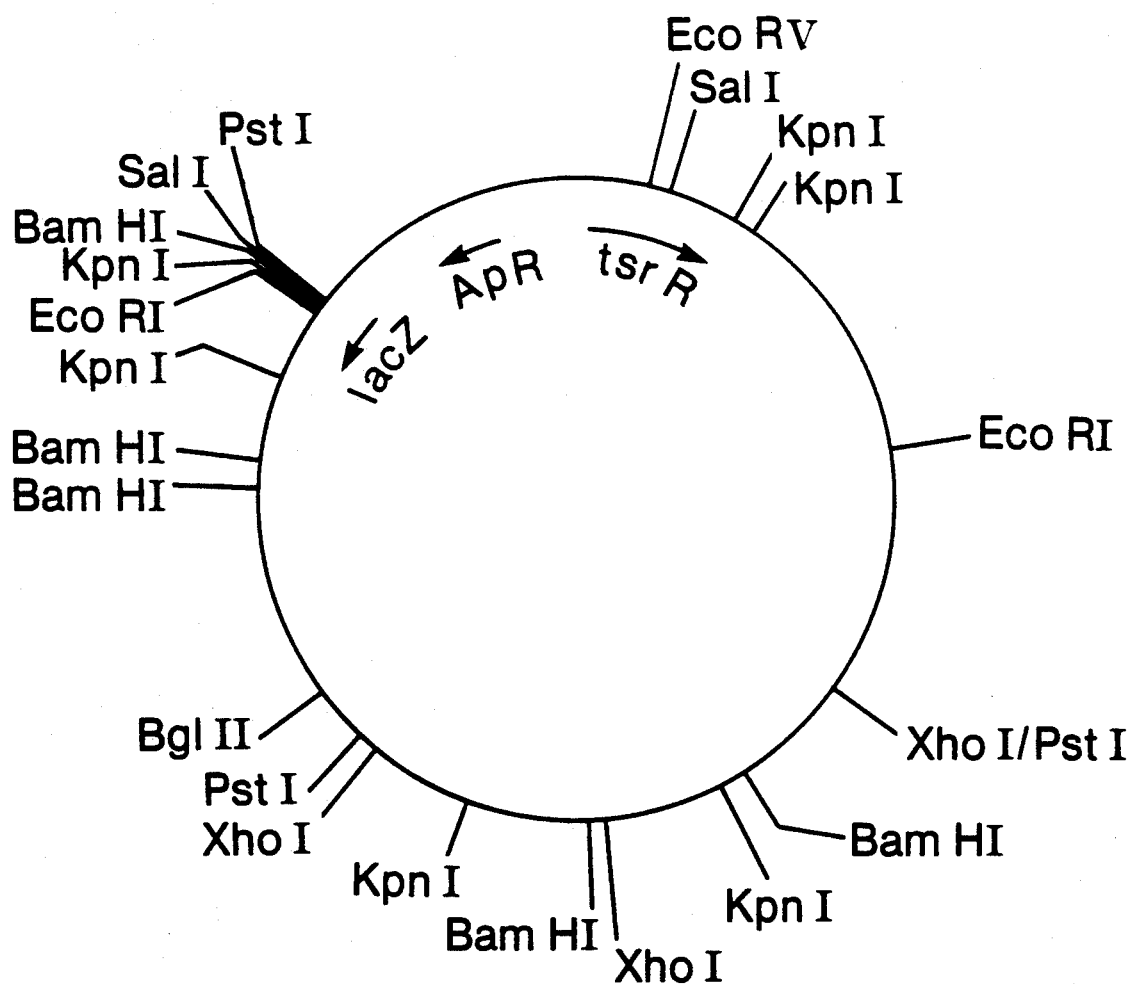
FIG. 4—Restriction Site and Function Map of Plasmid pKC668.

The EcoRI-digested, dephosphorylated plasmid pHJL401 DNA (1 μl) is added to 10 μl (~0.5 μg) of the EcoRI restriction fragment from pKC644, 2 μl of 10X ligase buffer (660 mM Tris-HCl, pH=8; 66 mM MgCl$_2$; 10 mM dithiothreitol (DTT); and 10 mM ATP), and 6 μl of H$_2$O. About 2 μl (1 unit/μl as defined by Boehringer-Mannheim, Indianapolis, Ind.) of T4 DNA ligase is added to the solution of DNA, and the resulting reaction is incubated at 15° C. overnight (~16 hours). The ligated DNA contains the desired plasmids pKC668 and pKC668A which differ only in the orientation of the ~10 kb EcoRI insert fragment. A restriction site and function map of plasmid pKC668 is presented in FIG. 4.

The EcoRI site on plasmid pHJL401 resides within a polylinker that itself forms part of the DNA sequence encoding the lacZ α-fragment. Expression of the lacZ α-fragment in an *E. coli* ΔM15 strain, such as *E. coli* K12 DH5α, restores the strain's ability to produce a functional β-galactosidase enzyme. Thus, plasmid pHJL401 can restore β-galactosidase activity to the *E. coli* K12 DH5α strain. However, insertion of DNA into a restriction site of the polylinker on plasmid pHJL401, as occurs in the construction of plasmid pKC668, disrupts the lacZ α-fragment coding sequence and concomitantly destroys the ability of the plasmid pHJL401; derivative to complement the ΔM15 mutation. β-galactosidase can hydrodyze X-Gal, which is 5-bromo-4-chloro-3-indolyl-β-D-galactopyranoside, a colorless compound, to an indigo-colored product and thus provides for a convenient screening method for discriminating between transformants containing starting plasmid pHJL401 and those containing a plasmid pHJL401 derivative, such as plasmid pKC668.

Frozen competent DH5α cells (Bethesda Research Laboratories, Inc. (BRL), P.O. Box 6009, Gaithersburg, Md. 20877) are transformed as per manufacturer's instructions. The cells are thawed on ice, 100 μl of cells are removed per transformation, and the unused cells are refrozen in a dry ice-ethanol bath. One μl of the ligation reaction mixture which has been diluted five-fold with water is added to 100 μl of cells pre-chilled on ice to 4° C. The cells are incubated on ice for 30 minutes, heat shocked at 42° C. for 45 seconds, and returned to ice for 2-5 minutes. One ml of SOC medium is added and the cells were incubated for one hour at 37° C. with shaking. SOC medium is 2% (w/v) tryptone, 0.5% (w/V) yeast extract, 20 mM glucose, 10 mM NaCl, 2.5 mM KCl, 10 mM MgCl$_2$, and 10 mM MgSO$_4$.

Aliquots of the transformation mixture are plated on L-agar plates containing 100 μg ampicillin/ml, 40 μg X-gal/ml, and 40 μg IPTG/ml. IPTG serves to derepress the lac promoter present on plasmid pHJL401. The plates are incubated at 37° C. overnight. Colonies that contain a plasmid without an insert, such as *E. coli* K12 DH5α/pHJL401, appear blue on these plates. Colonies that contain a plasmid with an insert, such as *E. coli* K12 DH5α/pKC668, are white. Several ampicillin-resistant, white colonies are selected and then screened by restriction enzyme analysis of their plasmid DNA. Plasmid DNA was obtained from the *E. coli* K12 DH5α/pKC668 transformants in accordance with the procedure for isolating plasmid pKC644 DNA, described above in Preparation 1, except that the cells are grown at 37° C. rather than 30° C. and are grown in broth containing 100 μg/ml ampicillin rather than apramycin. The plasmid pKC668 DNA can be used to transform Streptomyces, for example, *Streptomyces fradiae* GS14 (NRRL 12188), and *S. fradiae* GS50 (NRRL 12201), as described below.

B. Hybridization of plasmid pKC668 to *S. fradiae* DNA

An ~10 kb EcoRI fragment of pKC668 was isolated by treating pKC668 with restriction enzyme EcoRI in a manner analogous to that described above for pKC644. The fragment was labelled with α-$^{32}$P-dCTP using an oligonucleotide labelling kit (Pharmacia, 800 Centennial Avenue, Piscataway, N.J. 08854) following the manufacturer's instructions.

Two gels were run and transferred to a nylon membrane as described below:

The first gel contained BamHI cut DNA from *Streptomyces fradiae* strains including GS14 (tylA mutant) and GS50 (tylB mutant). The second gel contained BamHI and EcoRI digested DNA from plasmids/cosmids which contained inserts from *S. fradiae* chromoomal DNA. In particular, this gel contained restriction enzyme digested DNA from vectors which have been designated AUD 8-2, tlrC 8-6 and tlrC 8-1. The gels (0.8% agarose) in 1X TBE (0.089M Tris-borate, 0.089M boric acid, 0.002M EDTA) were run at 50 V for about 16.5 hours after which they were stained in ethidium bromide (1 μg/ml) in 1X TBE for 15 minutes, visualized under UV light and then photographed.

The gels then were washed in 0.25M HCl for 10 minutes at room temperature, then 1.5M NaCl and 0.5M NaOH for 30 minutes at room temperature and finally in 3.0M NaCl, 0.5M Tris-HCl (pH 8.0) for 30 minutes at room temperature. The DNA then was transferred by capillary action to nylon membranes (Hybond®, Amersham Corp., Chicago, Ill.) using 2X SSC (20X "SSC" is 3M NaCl, 0.3M sodium citrate). After the transfer, the gel is discarded and the nylon membrane is scrubbed in 2X SSC and 1% SDS. The DNA then is cross-linked to the membrane by exposure to UV light for 5 minutes.

The membranes are pre-hybridized for 2 hours at 45° C. in 10-25 ml of the following solution: 25 ml of 20X SSC, 22 ml of H$_2$O, 50 ml of deionized formamide, 1 ml of 10% SDS, 1 ml of 100X Denhardt's solution (4.0 g Ficoll (M.W. 40,000), 4.0 g polyvinylpyrollidone (M.W. 360,000), 4.0 g BSA and 200 ml H$_2$O) and 1 ml of sonicated denatured calf thymus DNA (5 mg/ml).

The hybridization is performed overnight at 45° C. with gentle agitation in 10 ml of the noted pre-hybridization solution supplemented with $1.5 \times 10^7$ cpm of the probe fragment which had been previously denatured. After the incubation, the membranes were washed at room temperature three times with 500 ml of 2X SSC and 0.1% SDS at about 15 minutes per wash. After this initial washing, the membranes were washed at 60° C. 3 times with 500 ml of 0.1X SSC, 0.1% SDS at about 15–30 minutes per wash. The membranes then were rinsed twice with 0.1X SSC at room temperature.

The membranes are exposed to X-ray film at −70° C. using intensifying screens. The ~10 kb EcoRI fragment of pKC668 was found to hybridize to two BamHI restriction fragments from the GS14 and GS50 DNA. The size of these fragments was ~8.7 kb and ~4.6 kb with the strongest hybridization to the ~8.7 kb fragment.

Further analysis showed that the ~10 kb EcoRI fragment of pKC668 hybridized to a region of ~9.8 kb of the *S. fradiae* genome. This region is bounded by an EcoRI site on AUD 8-2 and tlrC 8-6 and a BamHI site from tlrC 8-6 and tlrC 8-1. Fragments from these vectors served as a basis for further defining the tylosin biosynthetic genes of the invention.

EXAMPLE 1

Construction of Plasmid pSET551

A. Digestion of Cosmid AUD 8-2

About 10 μl (0.5 mg/ml) of cosmid AUD 8-2 were added to 10 μl of 10X PstI buffer (1M NaCl, 0.1M Tris-HCl (pH 7.5), 0.1M MgCl₂), 10 μg (1 mg/ml) of BSA, 5 μl (10 units/ml—New England Biolabs, Inc. 32 Tozer Road, Beverly, Mass.) of restriction enzyme PstI and 55 μl of water. The digestion was carried out at 37° C. for 2 hours after which 100 μl of phenol:chloroform:isoamyl alcohol (24:24:1) saturated with 1X TE buffer (10 mM Tris-HCl, pH 8.0, 1 mM EDTA) were added to the mixture. The digested cosmid was extracted by vortexing and spinning the mixture in a microcentrifuge for 2 minutes so as to separate the layers. The aqueous layer is removed and extracted with 100 μl of chloroform:isoamyl alcohol (24:1), the mixture centrifuged for 2 minutes to separate the layers after which the aqueous layer is removed. The DNA was precipitated from the aqueous layer by adding to the solution 10 μl of 3M sodium acetate and 250 μl of absolute ethanol. The mixture then was incubated at −70° C. for about 10 minutes after which the precipitate is collected by centrifugation for about 10 minutes. The DNA then was redissolved in 40 μl of water and 10 μl of 5X gel loading dye (50% glycerol in water, 50 mM EDTA, pH 8.0 0.25% bromophenol blue, 0.25% xylene cyanole). The DNA was loaded onto a 0.8% agarose gel in 1X TBE and eletrophoresed at 40 V for 16 hours. The gel was stained with 1 μg/ml ethidium bromide in 1X TBE for 15 minutes and the bands were visualized under ultraviolet light. A piece of DEAE cellulose (Schleicher and Schuell, NA-45 DEAE membrane) was embedded directly ahead of the 13 kb PstI fragment of AUD 8-2 by cutting out a small gel slice. This small gel slice is replaced and the 13 kb PstI fragment was electrophoresed onto the DEAE membrane at 150 V for 15–30 minutes. The membrane then was removed, washed in distilled water, placed in an 1.5 ml Eppendorf tube containing 400 μl NET buffer (1M NaCl, 0.1 mM EDTA, 20 mM Tris, pH 8.0), and incubated at 65° C. for 4 hours. The paper then was removed, 1 ml of absolute ethanol was added and the mixture was incubated at −20° C. overnight. The DNA was pelleted by centrifugation for 10 minutes and the pellet was resuspended in 50 μl of 1X TE buffer.

B. PstI Digestion of Plasmid pHJL401

Plasmid pHJL401, prepared in accordance with Preparation 2, above, was digested with restriction enzyme PstI as follows:

About 5 μg of plasmid pHJL401 (0.5 mg/ml) was combined with 5 μl of 10X PstI buffer, 5 μg of BSA (1 mg/ml) 3 μl (10 units/μl) of PstI restriction enzyme (New England Biolabs, Inc., 32 Tozer Road, Beverly, Mass.) and 27 μl of water. The digestion was carried out at 37° C. for 2 hours after which 50 μl of 50 mM Tris (pH 8.0) and 5 μl (2 units/μl) of calf intestinal alkaline phosphatase (Boehringer-Mannheim Biochemicals, P.O. Box 50816, Indianapolis, Ind. 46250) were added. This mixture was incubated at 37° C. for 30 minutes after which an additional 5 μl of alkaline phosphatase were added. The mixture then was incubated for 30 minutes at 37° C. After this incubation, 100 μl of phenol:chloroform:isoamyl alcohol (24:24:1) saturated with 1X TE buffer was added to the mixture. The mixture was vortexed and the aqueous phase was removed after centrifugation for 2 minutes. The aqueous phase was extracted with chloroform:isoamyl alcohol (24:1) and after centrifugation, the aqueous phase was removed. The DNA was precipitated from the mixture by incubating the aqueous phase at −20° C. for 10 minutes after having added 10 μl of 3M sodium acetate and 250 μl of absolute ethanol. The precipitate was pelleted by centrifugation and the pellet was resuspended in 100 μl of 1X TE buffer.

C. Ligation of PstI Digested pHJL401 with PstI Digested Cosmid AUD 8-2 (~13 kb Fragment)

The PstI digested dephosphorylated pHJL401 from above was diluted 1:10 in 1X TE buffer. Two μl of 10X ligation buffer (660 mM Tris-HCl, pH 8; 66 mM MgCl₂; 10 mM dithiothreitol (DTT); and 10 mM ATP) were added to 2 μl of the PstI digested solution, 10 μl of the ~13 kb PstI fragment from cosmid AUD 8-2 from above, and 2 μl of T4 DNA ligase (1 unit/μl; Boehringer-Mannheim, P.O. Box 50816, Indianapolis, Ind.) and 4 μl of H₂O. The mixture was incubated overnight at 15° C. After the incubation, 3 μl of 3M sodium acetate and 60 μl of absolute ethanol were added and the mixture was incubated at −20° C. for about 10 minutes. The precipitated DNA was pelleted by centrifugation and the pellet was resuspended in 10 μl of 1X TE.

As is the case for the EcoRI site on plasmid pHJL401, the PstI site on plasmid pHJL401 residues within a polylinker that itself forms part of the DNA sequence encoding the lacZ α-fragment. Expression of the lacZ α-fragment in an *E. coli* ΔM15 strain, such as *E. coli* K12 DH5α, restores the strain's ability to produce a functional β-galactosidase enzyme. Thus, plasmid pHJL401 can restore β-galactosidase activity to the *E. coli* K12 DH5α strain. However, insertion of DNA into a restriction site of the polylinker on plasmid pHJL401, as occurs in the construction of plasmid pSET551, pSET552, pSET556 or pSET555, as described below, disrupts the lacZ α-fragment coding sequence and concomitantly destroys the ability of the plasmid pHJL401 derivative to complement the ΔM15 mutation. β-galactosidase can hydrolyze X-Gal, which is 5-bromo-4-chloro-3-indolyl-β-D-galactopyranoside, a colorless compound, to an indigo-colored product and thus allows for a convenient screening method for discriminating between transformants containing starting plasmid pHJL401 and those containing a plasmid pHJL401 derivative, such as plasmid pSET551, pSET552, pSET555 or pSET556.

Thus, frozen competent DH5α cells (Bethesda Research Laboratories, Inc. (BRL), P.O. Box 6009, Gaithersburg, Md., 20877) were transformed as per manufactuer's instructions and as described in Preparation 3.

Aliquots of the transformations mixture were plated on L-agar plates containing 100 μg ampicillin/ml, 40 μg X-gal/ml, and 40 μg IPTG/ml. IPTG serves to derepress the lac promoter present on plasmid pHJL401. The plates were incubated at 37° C. overnight. Colonies that contain a plasmid without an insert, such as *E. coli* K12 DH5α/pHJL401, appear blue on these plates. Colonies that contain a plasmid with an insert are white. Twelve ampicillin-resistant, white colonies were selected and then screened by restriction enzyme analysis of the plasmid DNA. Plasmid DNA was obtained from the *E. coli* K12 DH5α transformants in accordance with the procedure for isolating plasmid pKC644 DNA, described in Preparation 1, except that the cells were grown at 37° C. rather than 30° C. and were growth in broth containing 100 μg/ml ampicillin rather than apramycin. One of the transformants contained a plasmid, designated as pSET551, which contained the desired construction. The restriction site and function map of pSET551 is shown in FIG. 5. Plasmid pSET551, transformed into host strain *E. coli* K12 DH5α, is available from the Agricultural Research Service, Northern Regional Research Laboratories ("NRRL"), under the accession number NRRL B-18411.

EXAMPLE 2

Construction of pSET552

Plasmid tlrC 4-3.24 contains *S. fradiae* DNA from the same region of the genome as cosmid tlrC 8-6, described in Preparation 3, above. This vector served as the source of the insert DNA for pSET552.

A. Preparation of EcoRI-BglII Restriction Fragments of *S. fradiae* DNA

The tlrC 4-3.24 DNA (37 μl) was combined with 5 μl of EcoRI buffer, 5 μl of 1 mg/ml BSA and 3 μl of restriction enzyme EcoRI (10 units/μl). The digestion was performed at 37° C. for 2 hours after which were added 5 μl of 3M sodium acetate and 150 μl of absolute ethanol. The DNA was allowed to precipitate at −70° C. for 30 minutes. The DNA was pelleted by centrifugation and resuspended in 74 μl H₂O.

The EcoRI digested DNA then was digested with BglII restriction enzyme by combining 37 μl of the EcoRI digested reaction mixture with 5 μl of BglII buffer (1M NaCl; 0.1M Tris-HCl (pH 7.4); 0.1M MgCl₂; 0.1M 2-merceptoethanol), 3 μl of BglII restriction enzyme (10 units/ml) and 5 μl of bovine serum albumin (1 mg/ml). This digestion is performed at 37° C. for 2 hours after which 50 μl of 1X TE buffer were added to the reaction mixture. The DNA then was extracted with 100 μl of TE buffer-saturated phenol:chloroform:isoamyl alcohol (24:24:1). After vortexing the mixture, the phases were separated by centrifugation. The aqueous phase was removed and extracted with 100 μl of chloroform:isoamyl alcohol (24:1). After vortexing and centrifugation, the aqueous phase was removed and 10 μl of 3M sodium acetate and 300 μl of absolute ethanol were added. After incubation at −70° C. for 30 minutes, the precipitated DNA was pelleted by centrifugation and the pellet was resuspended in 40 μl TE buffer.

B. EcoRI-BamHI Digestion of pHJL401

Plasmid pHJL401 was prepared according to the procedure outlined in Preparation 2. The vector then was digested with EcoRI restriction enzyme as previously described in Preparation 3. The EcoRI digested DNA then was digested with restriction enzyme BamHI in a manner analogous to that of the EcoRI digestion except that BamHI buffer (1.5M NaCl; 60 mM Tris-HCl (pH 7.9); 60 mM MgCl₂; 60 mM 2-mercaptoethanol) was substituted for EcoRI buffer and EcoRI restriction enzyme was replaced with BamHI endonuclease. The resulting fragments then were dephosphorylated using calf alkaline phosphatase as previously described.

After the digestion, the ~5.8 kb DNA fragment was separated by gel electrophoresis (0.8% agarose in TBE) at 40 volts for 16 hours and then purified as described in Example 1. The DNA obtained then was resuspended in 60 μl of TE buffer.

C. Ligation to Prepare Plasmid pSET552

The EcoRI-BglII digested tlrC 4-3.24 (20 μl) was combined with the EcoRI-BamHI digested pHJL401 from above and ligated with T4 DNA ligase in a manner analogous to that described in Example 1.

After ligation, the DNA obtained was transformed into *E. coli* K12 DH5α cells as described in Example 1. The transformed cells were plate on L-agar as described in Example 1. After incubation overnight at 37° C., 12 white colonies were selected and plasmid DNA was obtained from the transformants, substantially in accordance with the procedure described in Preparation 1. One of the transformants contained a plasmid, designated pSET552, which contained the desired construction. The restriction site and function map of pSET552 is shown in FIG. 6. Plasmid pSET552, transformed into host strain *E. coli* K12 DH5α, is available from the NRRL under the accession number NRRL B-18412.

EXAMPLE 3

Construction of Plasmid pSET555 and pSET556

Cosmid tlrC 8-6, as noted in Preparation 3, contains a DNA sequence which hybridizes with the *S. ambofaciens* DNA of pKC668 and which complements tylA and tylB mutant strains. This cosmid as well as pHJL401, were digested with restriction enzyme BamHI and the resulting fragments ligated to prepare plasmids pSET555 and pSET556. These latter vectors differ from each other only in the orientation of the inserted DNA.

A. BamHI Digestion of tlrC 8-6 and pHJL401

Each of the vectors was digested with restriction enzyme BamHI in a manner substantially as outlined in Example 2. The obtained DNA fragments (~8 kb from tlrC 8-6 and ~5.8 kb from pHJL401) were ligated and transformed into *E. coli* K12 DH5α using the procedures described in Examples 1 and 2. Twelve white, ampicillin-resistant colonies were selected and the DNA of each analyzed. The transformants contained the desired construction, and two plasmids designated pSET555 and pSET556, were selected for further analysis. The restriction site and function maps for pSET555 and pSET556 are shown in FIGS. 7 and 8, respectively. Each of these vectors were transformed into *E. coli* K12 DH5α and were deposited with the NRRL. These vectors are available from the Northern Regional Research Laboratories under the accession numbers NRRL B-18413 (pSET555) and NRRL B-18414 (pSET556).

EXAMPLE 4

Transformation and Tylosin Production in Streptomyces

The plasmids prepared in Examples 1 to 3 were isolated from the *E. coli* strains substantially in accordance with the procedure noted in Preparation 1 for the isolation of pKC644 DNA except the cultures were incubated at 37° C. instead of 30° C. and 100 μg/ml of ampicillin were used in place of apramycin. These plasmids then were transformed into Streptomyces, including the mutant strains *Streptomyces fradiae* GS5, GS14, GS50 and GS77. Complementation of each of these mutants strains verified the presence or absence of the tylA, tylB, tylG or TtylI genes of the invention, as previously described.

A. Transformation of Streptomyces

A culture of the desired Streptomyces strain was inoculated into 20 ml of trypticase-soya broth (TSB) and incubated in a water-bath incubator at 29° C. at 260 rpm overnight (about 16 hours). The culture was homogenized using a homogenizing vessel (Thomas Scientific, Swedesboro, N.J.) and a T-Line laboratory stirrer and then fragmented using a Sonifier Cell Disruptor (Heat Systems Ultrasonics, Inc.) for 7 seconds at 76 Watts. Four ml of the homogenized, fragmented culture were inoculated into 16 ml of TSB containing 0.3% weight by volume glycine, and the culture was again incubated overnight at 29° C. The following morning, the culture was homogenized and recultured as described above. After this third overnight incubation, the culture was homogenized, collected, and then washed twice with P medium. P medium is prepared by adding 103 g of sucrose to 0.25 g of $K_2SO_4$ and 2.03 g of $MgCl_2\cdot 6H_2O$ and then adding deionized water to a final volume of 700 ml. The mixture is then sterilized, and to each 70 ml of solution, about 10 ml each of 0.05 g $KH_2PO_4/100$ ml of deionized water; 2.78 g $CaCl_2/100$ ml of deionized water; and 0.25M TES (2-([tris-(hydroxymethyl)methyl]-amino)ethanesulfonic acid)) at pH=7.2 are added.

The cell pellet was resuspended in 15 ml of P medium containing 1 mg/ml lysozyme (Calbiochem, La Jolla, Calf. 92037) and then incubated at room temperature for about one-and-one half hours to form protoplasts. The protoplasts were gently collected by centrifugation, washed twice with P medium, resuspended in 2 ml of P medium, and incubated on ice until use. About 1 μg of the desired plasmid DNA was added to about 50 μl of 1 mg/ml heparin sulfate (Sigma) and incubated on ice for about 10 minutes. Much less plasmid DNA, about 5–100 nanograms, can be used to transform *Streptomyces fradiae* if prepared from a *S. fradiae* host. The procedure for isolating Streptomyces plasmid DNA is described in Hopwood et al., 1985, *Genetic Manipulation of Streptomyces: A Laboratory Manual* (John Innes Foundation, Norwich, England). The DNA/heparin solution was first added to about 200 μl of protoplasts, and about 0.9 ml of a solution composed of 55% PEG 1000 (Sigma) in P medium was then added to the DNA/protoplast mixture, and the resulting mixture was gently mixed at room temperature. The mixture was plate in varying aliquots onto R2 plates using 4 ml of soft-R2-agar overlays. R2 plates contain 30 ml of R2 medium and have been dried at 37° C. for about 4 days. R2 medium is prepared by adding 103 g sucrose, 0.25 g $K_2SO_4$, 2 ml of trace element solution, 10.12 g $MgCl_2\cdot 6H_2O$, 10.0 g of glucose, 2.0 g of L-asparagine, 0.1 g of Casamino acids, and 22 g of agar to 700 ml of water; sterilizing the resulting solution; and finally, adding 100 ml of each of the following solutions: 0.05 g $KH_2PO_4/100$ ml of deionized water; 2.22 g $CaCl_2/100$ ml of deionized water, and 0.25M TES pH=7.2. The pH of the final solution is adjusted to equal 7.2. Trace element solution contains 40 mg $ZnCl_2$, 200 mg $FeCl_3\cdot 6H_2O$, 10 mg $CuCl_2\cdot 2H_2O$, 10 mg $MnCl_2\cdot 4H_2O$, 10 mg $Na_2B_4O_7\cdot 10H_2O$, and 10 mg $(NH_4)_6Mo_7O_{24}\cdot 4H_2O$ per liter. The soft-R2-agar overlays are prepared by adding 51.5 g of sucrose, 5.06 g $MgCl_2\cdot 6H_2O$, 1.11 g $CaCl_2$, 50 ml of 0.25M TES at a pH=7.2, and 2.05 g agar to enough deionized water to achieve a final volume of 500 ml. The mixture is steamed to melt the agar, decanted into 4 ml aliquots, and autoclaved prior to use. After the transformed protoplasts had been plated, the plates were incubated at 29° C. for 24 hours, and then, 4 ml of soft-R2 agar containing 25 μl of 50 mg/ml thiostrepton (E. R. Squibb, Princeton, N.J. 08540) in DMSO were spread over the protoplasts. Incubation of the plates at 29° C. was continued until regeneration was complete, usually a period of about 7–14 days, to select for the desired *S. fradiae* transformants.

B. Tylosin-production in the Transformed Strains

The transformed *Streptomyces fradiae* strains were cultured and complementation of the strains carrying mutant genes was determined by assaying for tylosin production (or demycinosyltylosin in the case of complementation of the tylI mutation in GS77) in substantial accordance with the methods described in Baltz and Seno, 1981, *Antimicrobial Agents and Chemotherapy* 20:214–225.

In particular, the transformed stains were cultured in fermentation medium (Baltz and Seno, 1981, *Antimicrobial Agents and Chemotherapy* 20:214–225) that also contained 20 μg/ml thiostrepton if the strain being cultured harbored a plasmid. The transformed mutant strains, GS5, GS14, GS50 and GS77 are low tylosin-producing, or produce amounts of tylosin that are not readily detectable, and were cultured in the presence of selective pressure (thiostrepton) for plasmid maintenance as an autonomously replicating vector.

The noted transformants can be converted to integrants, transformants in which all or part of the plasmid DNA has integrated into the genome of the host cell. Two methods are used to obtain integrants. In the first method, transformants are passaged onto selective (contains thiostrepton) and nonselective plates and incubated about 7 days at 29° C. to obtain growth patches. The patches on the nonselective plates that were thiostrepton-resistant on the selective plate are repassaged several times in the same manner until a single colony was found to be relatively stable without selection. In the second method for obtaining integrants, the transformants are nonselectively passaged several times by transferring spores from the surface of the plate using a cotton swab. After several passages, the colonies are grown in non-selective, liquid medium (TSB), homogenized, fragmented by sonication, diluted, and plated on selective and nonselective medium to identify relatively stable integrants. Other methods of obtaining stable integrants will be apparent to those skilled in the art.

Relatively stable integrants are used to inoculate vegetative medium (complex vegetative medium contains, per liter, 10 g of corn steep liquor, 5 g of yeast extract, 5 g of soybean grits, 3 g of calcium carbonate, and 4.5 g of crude soybean oil, and the pH is adjusted to 7.8 with NaOH). If stable transformants are obtained, then TSB without thiostrepton (no selective pressure) is also a suitable vegetative medium. If stable transformants are not obtained, thiostrepton to maintain selective pressure should be used in both the vegetative and fermentation medium (defined below). The vegetative culture then is used to inoculate (10% inoculum) the fermentation medium, which also lacked thiostrepton (subject to the note above).

Tylosin fermentation medium consists of beet molasses (2%), corn meal (1.5%), fish meal (0.9%), corn gluten (0.9%), sodium chloride (0.1%), ammonium phosphate (dibasic) (0.04%), calcium carbonate (0.2%), and crude soybean oil (3%). The pH of the medium is adjusted with 1N NaOH to 7.1. Fermentations are run at 260 rpm at 29° C. for seven days. The total macrolide content of the fermentation broth is measured by extraction with methanol:CHCl$_3$, reading the absorbance at 290 nm, and comparing to a standard curve. Tylosin factors are identified by spotting the fermentation broth onto silica-gel-TLC plates and developing the plates with a solvent system of 95:5 ethylacetate: diethylamine. The concentration of individual macrolide components is the total A$_{290}$ times the percentage of each component as determined by HPLC.

Table V outlines the levels of tylosin production observed when the plasmids of the invention are transformed into mutant strains GS5, GS14, GS50, and GS77, as outlined above.

TABLE V

Restoration of Tylosin or Demycinosyltylosin Production by Complementation or Repair of tyl Mutations by Cloned tyl Genes

| Mutant | Genotype | Plasmid | mg/ml Tylosin | DMT |
|---|---|---|---|---|
| GS5 | tylG | none | <0.01 | |
| | | pHJL401 | <0.01 | |
| | | pSET551 | 1.18 | |
| | | pSET552 | <0.01 | |
| | | pSET555 | 0.86 | |
| | | pSET556 | 0.58 | |
| GS14 | tylA | none | 0.01 | |
| | | pHJL401 | <0.01 | |
| | | pSET551 | <0.01 | |
| | | pSET552 | 2.70 | |
| | | pSET555 | 0.48 | |
| | | pSET556 | 0.40 | |
| GS50 | tylB | none | <0.01 | |
| | | pHJL401 | <0.01 | |
| | | pSET551 | <0.01 | |
| | | pSET552 | 1.48 | |
| | | pSET555 | 0.59 | |
| | | pSET556 | 0.78 | |
| GS77 | tylD, tylI | none | | <0.01 |
| | | pHJL401 | | <0.01 |
| | | pSET551 | | 0.73 |
| | | pSET552 | | 0.81 |
| | | pSET555 | | N.T.* |
| | | pSET556 | | 0.58 |

In the absence of complementation of the tylD mutation, demycinosyltylosin (DMT) is the final product expected by complementation of the tylI mutation in GS77 (see K. L. Cox, et al., J. Nat. Prod. 49, 971 (1986).
*N.T. = not tested

We claim:

1. An isolated DNA sequence which comprises a gene sequence which encodes an activity selected from the group consisting of the tylA, tylB and tylI biosynthetic gene products of *Streptomyces fradiae*.

2. An isolated DNA sequence as claimed in claim 1 comprising a gene sequence which encodes the tylA gene product of *Streptomyces fradiae*.

3. An isolated DNA sequence as claimed in claim 1 comprising a gene sequence which encodes the tylB gene product of *Streptomyces fradiae*.

4. An isolated DNA sequence as claimed in claim 1 comprising a gene sequence which encodes the tylI gene product of *Streptomyces fradiae*.

5. A DNA sequence as claimed in claim 2 which comprises the ~9.8 kb EcoRI-BglII fragment of pSET552, the ~8.6 kb BamHI fragment of pSET555, or the ~8.6 kb BamHI fragment of pSET556.

6. A DNA sequence as claimed in claim 2 which comprises the ~6.2 kb EcoRI-PstI fragment of plasmid pSET552.

7. A DNA sequence as claimed in claim 3 which comprises the ~9.8 kb EcoRI-BglII fragment of pSET552, the ~8.6 kb BamHI fragment of pSET555, or the ~8.6 kb BamHI fragment of pSET556.

8. A DNA sequence as claimed in claim 3 which comprises the ~6.2 kb EcoRI-PstI fragment of plasmid pSET552.

9. A DNA sequence as claimed in claim 4 which comprises the ~13 kb PstI fragment of pSET551, the ~9.8 kb EcoRI-BglII fragment of pSET552, the ~8.6 kb BamHI fragment of pSET555, or the ~8.6 kb BamHI fragment of pSET556.

10. A DNA sequence as claimed in claim 4 which comprises the ~1.4 kb EcoRI-PstI fragment of plasmid pSET551, pSET552, pSET555, or pSET556.

11. A recombinant DNA vector which comprises a DNA sequence as claimed in claim 1.

12. A recombinant DNA vector as claimed in claim 11 which is an expression vector.

13. A recombinant DNA vector as claimed in claim 11 which is a plasmid.

14. A plasmid as claimed in claim 13 which is selected from the group consisting of plasmids pSET551, pSET552, pSET555 and pSET556.

15. A host cell transformed with a recombinant vector as claimed in claim 11.

16. A host cell transformed with a recombinant vector as claimed in claim 12.

17. A host cell transformed with a recombinant vector as claimed in claim 13.

18. A host cell transformed with a recombinant vector as claimed in claim 14.

19. A host cell as claimed in claim 15 which is Streptomyces.

20. A host cell as claimed in claim 19 which is *Streptomyces fradiae*.

21. The *Streptomyces fradiae* as claimed in claim 20 which is *S. fradiae* GS14, *S. fradiae* GS50 or *S. fradiae* GS77.

22. A host cell as claimed in claim 15 which is *E. coli*.

23. A host cell as claimed in claim 22 which is *E. coli* K12 DH5α.

24. A transformed host cell which is selected from the group consisting of *E. coli* DH5α/pSET551, *E. coil* DH5α/pSET552, *E. coli* DH5α/pSET555 and *E. coli* DH5α/pSET556.

25. A method for increasing the tylosin-producing ability of a tylosin-producing microorganism, said method comprising
 1) transforming with a recombinant DNA vector or portion thereof a microorganism that produces tylosin or a tylosin precursor by means of a biosynthetic pathway, said vector or portion thereof comprising a DNA sequence as claimed in claim 1 that codes for the expression of an activity that is rate limiting in said antibiotic biosynthetic pathway, and
 2) culturing said microorganism transformed with said vector under conditions suitable for cell growth, expression of said antibiotic biosynthetic gene, and production of said antibiotic or antibiotic precursor.

26. A method as claimed in claim 25 in which the vector or portion thereof comprises a DNA sequence encoding the tylA gene product.

27. A method as claimed in claim 25 in which the vector or portion thereof comprises a DNA sequence encoding the tylB gene product.

28. A method as claimed in claim 25 in which the vector or portion thereof comprises a DNA sequence encoding the tylI gene product.

* * * * *